US012706076B2

(12) United States Patent
Choy et al.

(10) Patent No.: US 12,706,076 B2
(45) Date of Patent: Aug. 11, 2026

(54) METHOD AND SYSTEM FOR CONTROLLING NOISE

(71) Applicants: Innovation Technology Company Limited, Hong Kong (CN); THE HONG KONG POLYTECHNIC UNIVERSITY, Hong Kong (CN); The Education University of Hong Kong, Hong Kong (CN)

(72) Inventors: Yat Sze Choy, Hong Kong (CN); Wai Yin Mung, Hong Kong (CN); Che Hin Chan, Hong Kong (CN); Shun Ming Yuen, Hong Kong (CN); Ka Ming Wu, Hong Kong (CN); Ho Man Yu, Hong Kong (CN); Tak Chun Kwong, Hong Kong (CN)

(73) Assignees: Innovation Technology Company Limited, Hong Kong (CN); The Hong Kong Polytechnic University, Hong Kong (CN); The Education University of Hong Kong, Hong Kong (CN)

( * ) Notice: Subject to any disclaimer, the term of this patent is extended or adjusted under 35 U.S.C. 154(b) by 279 days.

(21) Appl. No.: 18/414,752

(22) Filed: Jan. 17, 2024

(65) Prior Publication Data

US 2025/0232752 A1 Jul. 17, 2025

(51) Int. Cl.
*G10K 11/178* (2006.01)
*A61B 5/372* (2021.01)

(52) U.S. Cl.
CPC ........ *G10K 11/17815* (2018.01); *A61B 5/372* (2021.01); *G10K 11/17823* (2018.01); *G10K 11/17825* (2018.01); *G10K 11/17881* (2018.01); *G10K 2210/1081* (2013.01); *G10K 2210/3012* (2013.01); *G10K 2210/3016* (2013.01); *G10K 2210/3026* (2013.01); *G10K 2210/3027* (2013.01); *G10K 2210/3028* (2013.01)

(58) Field of Classification Search
CPC ..... G10K 11/17881; G10K 2210/1081; G10K 11/17823; G10K 11/1781; H04R 2460/01; H04R 1/1083
See application file for complete search history.

(56) References Cited

U.S. PATENT DOCUMENTS

| | | | | |
|---|---|---|---|---|
| 2018/0254033 | A1* | 9/2018 | Davi | G10K 11/17881 |
| 2019/0175961 | A1* | 6/2019 | Awiszus | A61F 9/067 |
| 2021/0306772 | A1* | 9/2021 | Wiss | H04R 25/652 |
| 2023/0245638 | A1* | 8/2023 | Veselinovic | G10K 11/17823 381/66 |
| 2024/0122525 | A1* | 4/2024 | Gilron | A61B 5/7275 |

OTHER PUBLICATIONS

American Psychiatric Association, Diagnostic and statistical manual of mental disorders: DSM-5, American Psychiatric Association, Arlington, 2013.

(Continued)

*Primary Examiner* — Kile O Blair

(57) ABSTRACT

A method for controlling noise for a human subject comprise receiving an acoustic signal by the human subject through a headphone, the acoustic signal comprising a noise signal, generating a cancellation signal based on a hearing target curve that is related to acoustic magnitude and frequency, and applying the cancellation signal to the acoustic signal such that the noise signal is attenuated.

17 Claims, 19 Drawing Sheets

(56) References Cited

OTHER PUBLICATIONS

X. Sun, C. Allison, F.E. Matthews, S.J. Sharp, B. Auyeung, S. Baron-Cohen, and C. Brayne, Prevalence of autism in mainland China, Hong Kong and Taiwan: A systematic review and metaanalysis, Mol. Autism 4 (1) (2013) 7, https://doi.org/10.1186/2040-2392-4-7.

S.L. Bishop, V. Hus, A. Duncan, M. Huerta, K. Gotham, A. Pickles, A. Kreiger, A. Buja, S. Lund, C. Lord, Subcategories of restricted and repetitive behaviors in children with autism spectrum disorders, J. Autism Dev. Disord. 43 (6) (2012) 1287-1297, https://doi.org/10.1007/s10803-012-1671-0.

J.R. Lucker, Auditory hypersensitivity in children with autism spectrum disorders, Focus Autism Dev. Dis. 28 (3) (2013) 184-191, https://doi.org/10.1177/1088357613475810.

S. Khalfa, N. Bruneau, B. Rogé, N. Georgieff, E. Veuillet, J.-L. Adrien, C. Barthélémy, L. Collet, Increased perception of loudness in autism, Hearing Res. 198 (1-2) (2004) 87-92, https://doi.org/10.1016/j.heares.2004.07.006.

M.W. Kuiper, E.W. Verhoeven, H.M. Geurts, Stop making noise! auditory sensitivity in adults with an autism spectrum disorder diagnosis: Physiological habituation and subjective detection thresholds, J. Autism Dev. Disord. 49 (5) (2019) 2116-2128, https://doi.org/10.1007/s10803-019-03890-9.

Y.-H. Tan, C.-Y. Xi, S.-P. Jiang, B.-X. Shi, L.-B. Wang, L. Wang, Auditory abnormalities in children with autism, Open J. Psychiat. 2 (1) (2012) 33-37, https://doi.org/10.4236/ojpsych.2012.21005.

R. Ferri, M. Elia, N. Agarwal, B. Lanuzza, S.A. Musumeci, G. Pennisi, The mismatch negativity and the P3A components of the auditory event-related potentials in autistic low-functioning subjects, Clin. Neurophysiol. 114 (9) (2003) 1671-1680, https://doi.org/10.1016/s1388-2457(03)00153-6.

L. Zhang, J. Tao, X. Qiu, Active control of transformer noise with an internally synthesized reference signal, J. Sound Vib. 331 (15) (2012) 3466-3475, https://doi.org/10.1016/j.jsv.2012.03.032.

L. Wu, X. Qiu, I.S. Burnett, Y. Guo, A recursive least square algorithm for active control of mixed noise, J. Sound Vib. 339 (2015) 1-10, https://doi.org/10.1016/j.jsv.2014.11.002.

S. Baron-Cohen, R. A. Hoekstra, R. Knickmeyer, S. Wheelwright, The autism-spectrum quotient (AQ)-adolescent version, J. Autism Dev. Disord. 36 (3) (2006) 343-350, https://doi.org/10.1007/s10803-006-0073-6.

H. Tiitinen, P. Sivonen, P. Alku, J. Virtanen, R. Näätänen, Electromagnetic recordings reveal latency differences in speech and tone processing in humans, Cognitive Brain Res. 8 (3) (1999) 355-363, https://doi.org/10.1016/s0926-6410(99)00028-2.

J.S. Gravel, M. Dunn, W.W. Lee, M.A. Ellis, Peripheral audition of children on the autistic spectrum, Ear Hearing 27 (3) (2006) 299-312, https://doi.org/10.1097/01.aud.0000215979.65645.22.

* cited by examiner

METHOD AND SYSTEM FOR CONTROLLING NOISE

FIELD OF THE DISCLOSURE

The present disclosure generally relates to noise control in relation to acoustic signals that are received into human ears.

BACKGROUND

Autism spectrum disorder (ASD) is a neurodevelopmental condition characterized by deficits in social interaction and communication, and repetitive, restricted and stereotyped patterns of behaviour. It is accompanied by various sensory features such as hyper- or hypo-reactivity to sensory input, etc. When people with autism who are sensitive to sound perceive unpleasant auditory stimuli, not only would it result in strong reactions but it could also result in reduced engagement in important life activities and avoidance of specific environments and interactions. Existing environmental noise control methods include controlling the sound propagation path, for example, by installing noise-absorbing panels, and designating a quiet zone by erecting a barrier. Existing systems and methods also include earmuffs and portable noise-cancelling headphones for controlling noise directly at the receiver. They provide a barrier between ears and external environment It is an object of the present disclosure to overcome or substantially ameliorate one or more of the disadvantages of prior art, or at least to provide a useful alternative.

SUMMARY

In one aspect of the disclosure there is provided a method for controlling noise for a human subject. The method comprises receiving an acoustic signal by the human subject through a headphone, the acoustic signal comprising a noise signal; generating a cancellation signal based on a hearing target curve that is related to acoustic magnitude and frequency; and applying the cancellation signal to the acoustic signal such that the noise signal is attenuated.

Additionally or optionally, the hearing target curve comprises a relationship between noise attenuation in decibel (dB) and acoustic frequency. The acoustic frequency may be in a range from 250 Hz to 8000 Hz.

Additionally or optionally, the method further comprising: determining, based on a hearing perception curve, a sound intensity hearing level that corresponds to a neutral response for the human subject; and computing the noise attenuation based on a difference between the sound intensity hearing level and a noise level.

Additionally or optionally, the method further comprises determining the neutral response by performing a power function curve fitting $$y_i = a(x_i^b) + c,$$

where $y_i$ is an ith mean perception rating, $x_i$ is an ith intensity level, a, b, c are coefficients.

Additionally or optionally, the method further comprises performing a clustering algorithm on a plurality of human subjects. The clustering algorithm may comprise an agglomerative hierarchical algorithm.

Additionally or optionally, the method comprises performing electroencephalography test on the plurality of human subjects to obtain neural response of the plurality of human subjects in response to sound stimuli.

Additionally or optionally, the method further comprises: recording data measured by the electroencephalography test; re-referencing the data to obtain re-referenced data; filtering the re-referenced data to obtain filtered data; and determining a search window to identify a first peak P1, a second peak P2, and a trough point N1.

Additionally or optionally, the method comprises performing baseline correction on the filtered data. The method may further comprise averaging the filtered data in the search window.

Additionally or optionally, the method further comprises: configuring the acoustic signal such that the acoustic signal travels along a primary path and evolves into a residual signal; and performing superposition of the residual signal and the cancellation signal to generate an error signal.

Additionally or optionally, the method further comprises: measuring the error signal; computing a difference between the acoustic signal and the error signal; and comparing the difference and the cancellation signal. If the difference and the cancellation signal is greater than a threshold, the method tunes at least one parameter of an adaptive filter.

In another aspect of the disclosure there is provided a system for controlling noise for a human subject. The system comprises a headphone configured to receive an acoustic signal and a computer device. The computer device is configured to generating a cancellation signal based on a hearing target curve that is related to acoustic magnitude and frequency, and apply the cancellation signal to the acoustic signal such that the noise signal is attenuated.

Additionally or optionally, the system further comprises a primary path configured to transmit the acoustic signal such that the acoustic signal evolves into a residual signal, and a secondary path configured to transmit the cancellation signal. Superposition operation is performed for the residual signal and the cancellation signal at an intersection of the primary path and a secondary path such that an error signal is generated. An adaptive filter may be disposed on the secondary path Additionally or optionally, the headphone comprises a reference microphone configured to measure the acoustic signal; and an error microphone configured to measure the error signal.

Additionally or optionally, the computer device computes a difference between the acoustic signal and the error signal, and compares the difference and the cancellation signal. The computer device may further tune at least one parameter of the adaptive filter when the difference and the cancellation signal is greater than a threshold.

Other example embodiments are discussed herein.

BRIEF DESCRIPTION OF THE DRAWINGS

Embodiments of the disclosure will now be described, by way of example only, with reference to the accompanying drawings in which.

DETAILED DESCRIPTION

Figure 1A:
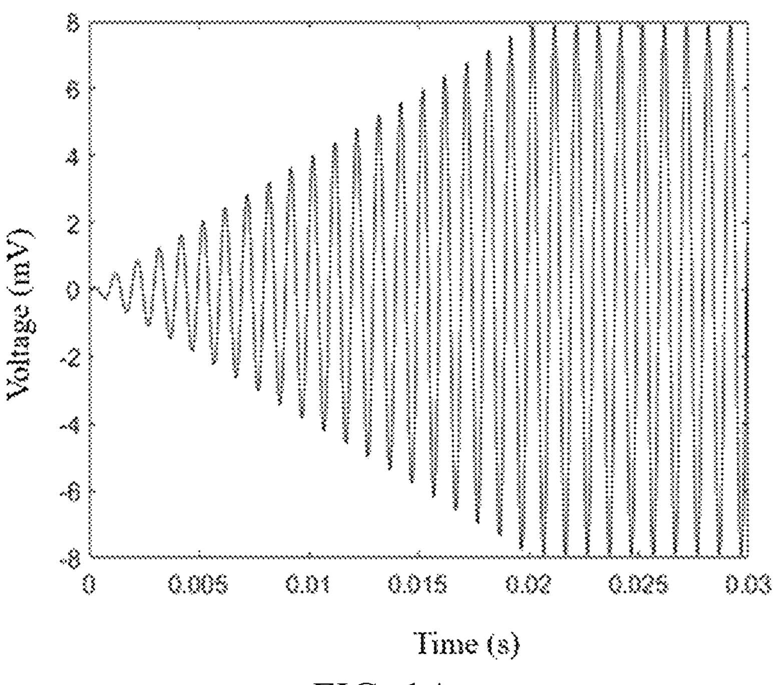
FIG. 1A illustrates an example of tonal sound with duration of 1 second (s) and 20 milliseconds (ms) onset/offset ramp according to certain embodiments of the present disclosure.

The present disclosure will now be described with reference to the following examples which should be considered in all respects as illustrative and non-restrictive. In the Figures, corresponding features within the same embodiment or common to different embodiments have been given the same or similar reference numerals.

Throughout the description and the claims, the words “comprise”, “comprising”, and the like are to be construed in an inclusive sense as opposed to an exclusive or exhaustive sense; that is to say, in the sense of “comprising, but not limited to”.

Furthermore, as used herein and unless otherwise specified, the use of the ordinal adjectives “first”, “second”, etc., to describe a common object, merely indicate that different instances of like objects are being referred to, and are not intended to imply that the objects so described must be in a given sequence, either temporally, spatially, in ranking, or in any other manner.

Example embodiments relate to method and system for controlling noise that take account for individual aural sensations of human subjects. A human subject as described herein may be a person with autism or hearing problems, or a normal person that expects to avoid unexpected or undesirable noises. Albeit in the following, embodiments of the present discourse may be described with reference to those with autism, it will be appreciated that the present disclosure can be applicable to people without autism or other physical or mental issues.

Many existing systems or methods are flawed in one or more aspects. For example, some use a fixed noise suppression facility at one location, which is unsuitable for human beings who move around and undertake activities in different locations in their daily lives. The existing technologies do not consider influence of the physical properties of the sound, including the frequency and sound intensity level. The performance of many existing systems is poor in low frequency region. Some technologies are based on suppression of the sound pressure level only, and use a same type of noise cancelling function for all the human subjects without considering their individual aural sensations.

Example embodiments solve one or more of these problems associated with the existing technologies and provide technical solutions with novel designs.

According to one or more embodiments, to design a suitable noise-control function in headphones to cater to those with autism and having different aural perceptions, a series of aural perception and electroencephalography (EEG) tests are conducted, where autistic participants with auditory hyperreactivity listen to sounds of different frequencies and amplitudes such that their subjective aural responses can be analysed. Suitable noise-attenuation target curves or hearing target curve are determined based on hearing perception curves that are constructed as a function of the mean aural perception ratings and noise levels using power function fitting. Subsequently, a hybrid active noise cancellation (ANC) system based on aural perception is developed and validated. The results shows that frequencies of 250 Hz and 8 kHz are rated by the majority of the participants with autism as most unpleasant. By way of example, the participants are partitioned into five clusters using the K-means algorithm. Each cluster is found to have its own characteristic aural perception response. Ultimately, an improvement in the aural perception response is observed when the participants use this type of headset or headphone that has aural perception characteristics suitable for different clusters of participants with autism. Albeit the participants as described herein are children or teenagers, it will be understood that they are mere examples of human subjects and for illustrative purpose only. In some embodiments, the participants may be people at other age groups.

According to one or more embodiments, subjective aural perception and EEG tests with different sound stimuli are conducted on participants with autism and typical development such that the aural perception response and characteristics of these participants subjected to sound stimuli of various frequencies and magnitudes can be understood and quantified. There is correlation between aural perception rating and the amplitude of the slow-wave cortical auditory evoked potentials. Generally, autistic participants in all the clusters feel unpleasant, particularly at 250 Hz and 8 kHz, although the perception rating obtained varies according to the noise level. Different clusters have their own characteristics of frequency and sound intensity hearing level responses subject to sound stimuli. This indicates that the need for noise control to address specific frequencies causes annoyance in different participants at different levels. An active noise control system in a headset or headphone with the function of aural perception response is developed to alleviate the adverse aural behaviours of participants with autism, and its performance and improvement are validated through experiments and surveys.

To design a suitable noise control function in headphones to cater to participants with autism having different aural perceptions, one or more embodiments of the present disclosure investigate the aural response of participants with autism and auditory hyperreactivity in terms of amplitude and frequency, establish an assessment method that can quantify the perception of sound of the autistic participants, determine the relationship between the physical parameters of sound and the subjective aural response, and develop a suitable human perception ANC approach to effectively alleviate the adverse behaviours related to auditory hyperreactivity in participants with autism.

To illustrate the inventive concept and demonstrate how the inventive concept is implemented, in the following, experiments according to certain embodiments are described and discussed. In the experiments, children or teenagers with or without autism are participants. It will appreciated that the experiments, including various numeral values, numbers, etc. used or selected, are for illustrative purpose only, and by no means should be understood as limiting.

By way of example, to understand the aural sensation in participants with autism, and the differences between participants with and without autism, the assessment of their acoustic responses is conducted in two sessions. The first session is focused on the subjective evaluation experiment, which directly reflects the subjective aural perception or response of different sound stimuli or excitation. The second session includes physiological acoustic response that reflects the intermediate neural response to sound excitation and its corresponding emotion.

There are two groups of participants: typical growth participants (TD) and participants with autism (ASD), where participants in the TD group do not have autism. A total of 83 ASD participants (seventy-five males and eight females, with a mean age of 9±1.7 years) and 50 TD participants (thirty-eight males and nineteen females, with a mean age of 10±1.4 years) are recruited by means of purposive and snowball sampling. The recruited participants with autism are diagnosed with autism, autistic disorder, or Asperger's syndrome and complete the Hong Kong version of Autism Spectrum Quotient aged 7-12 years and with primary education. Participants are able to respond verbally using a five-point Likert scale. The normal hearing function of these participants is assessed using a hearing ability test with pure tone audiometry. For the hearing ability test, all the participants are screened twice for their hearing threshold at 250 Hz, 500 Hz, 1000 Hz, 2000 Hz, 3000 Hz, 4000 Hz, and 8000 Hz with three different sound-intensity hearing levels (10, 15, and 20 dB HL). Participants are asked to indicate verbally or through gestures whether they can hear a sound delivered by the headphones. The average hearing level of the participants over all the measured frequencies is higher than the acceptable level of 15 dB HL. In addition, these participants score 85 or higher on the Test of Nonverbal Intelligence, Fourth Edition (TONI-4). To obtain their neural responses upon sound or acoustic excitation, the participants are confirmed to have no neurological disorders. The autistic participants also complete an auditory hyperreactivity screening using the Chinese version of the Sensory Profile or auditory hyperreactivity, according to which scores of 30 or less are defined as having auditory hyperreactivity.

Figure 1B:
FIG. 1B illustrates a calibration setup of a sound stimuli presentation system according to certain embodiments of the present disclosure.

To obtain the acoustic perception and aural responses of the two groups of participants, the sound stimuli are focused on tonal signals with different frequencies and amplitudes. The full set of sound stimuli comprises 36 sound tracks, with six different frequencies (0.25 kHz, 0.5 kHz, 1 kHz, 2 kHz, 4 kHz, and 8 kHz) and six different sound intensity hearing levels (30, 40, 50, 60, 70, and 78 dB HL), where dB HL is the decibels in hearing level commonly used in audiology, wherein 0 dB HL is the average hearing threshold in dB sound pressure level for the average, normal-hearing listener. These six centre octave frequencies cover almost the entire frequency range of environmental sounds in the community. Each tonal sound with a corresponding amplitude is generated for a duration of 1 s and a 20-ms onset/offset ramp, as shown in FIG. 1A. The entire set of acoustic stimuli with the aforementioned frequencies and amplitudes is repeated thrice. The equipment used for the sound stimuli presentation is calibrated using a head and torso simulator to ensure the accurate delivery of sound stimuli. The calibration setup is shown in FIG. 1B, which shows a head and torso simulator 102 and a signal conditioner 104.

Figure 2:
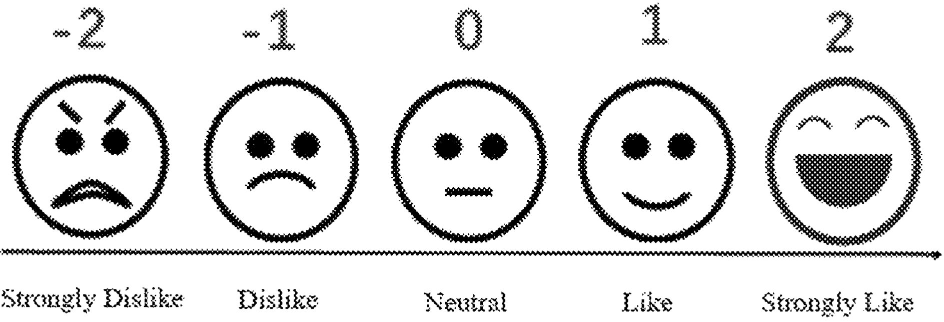
FIG. 2 illustrates a five-point Likert scale with the corresponding emoticon adopted in an aural perception test according to certain embodiments of the present disclosure.

The subjective aural perception or response of the participants is evaluated in a soundproof chamber. During the experiment, sound stimuli are played using a computer connected to Bose QC35II headphones with an audio amplifier. The experiment control software E-Prime 2.0 is utilised to create a randomised sound stimuli sequence for each participant. This enables researchers to record participants' responses using a response recorder in the form of a response pad without them knowing the sound stimuli sequence in advance. In addition, the software allows researchers to insert an interstimulus interval (which is a time interval with silence in this experiment) with varying durations based on the participants' responses after each sound stimulus. The procedure for presenting each sound stimulus is as follows. Before the presentation of each sound stimulus, a black fixation cross appears at the centre of the screen to capture the participant's attention. After the sound is played, each participant is presented with a five-point Likert scale along with the corresponding emoticon, as shown in FIG. 2. The Likert scale is designed as a bipolar scale to capture both the pleasant and unpleasant feelings of the participants when listening to sound stimuli. The participants are asked to verbally rate how much they liked or disliked the sound. The ratings are +2 representing 'strongly like' with a broadly smiling face emoticon, +1 representing 'like' with a smiling face emoticon, 0 representing 'neutral' with a neutral face emoticon, −1 representing 'dislike' with a sad face emoticon, and −2 representing 'strongly dislike' with a very sad face emoticon on the display. If a participant does not hear a sound, the researcher will repeat it. The interstimulus intervals are between 2 s and 10 s, depending on the participant's response, to avoid habituation effects. For trials with ratings of −1 (dislike) or −2 (strongly dislike), the intervals varies between 8 and 10 s. The interval is 5 s for trials with a rating of 0 (neutral). For trials with ratings of +1 (like) or +2 (strongly like), the intervals varies between 2 and 4 s. The entire set of sound stimuli consists of 36 sound stimuli, which are repeated thrice at random to check the repeatability. The total experiment duration is approximately 30 minutes (min).

Figure 3A:
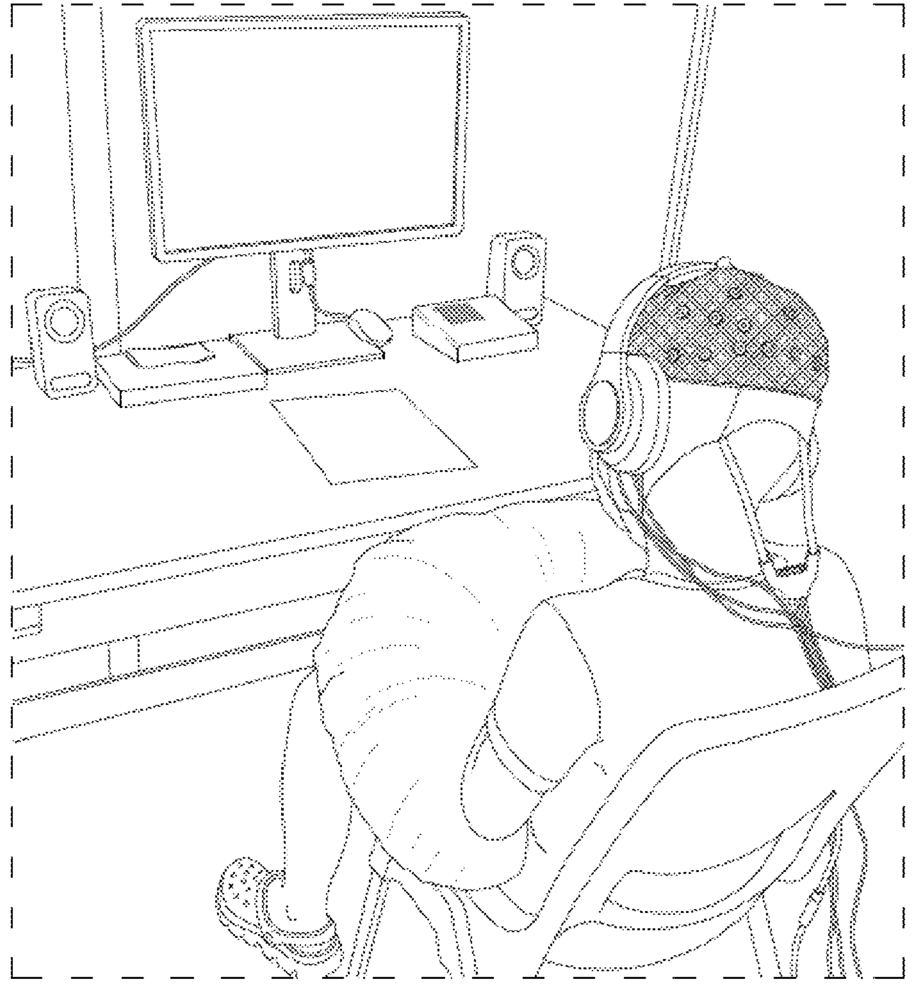
FIG. 3A illustrates a participant of an electroencephalography (EEG) test wearing a EEG cap to record raw EEG signals while listening to sound stimuli from a headphone according to certain embodiments of the present disclosure.
Figure 3B:
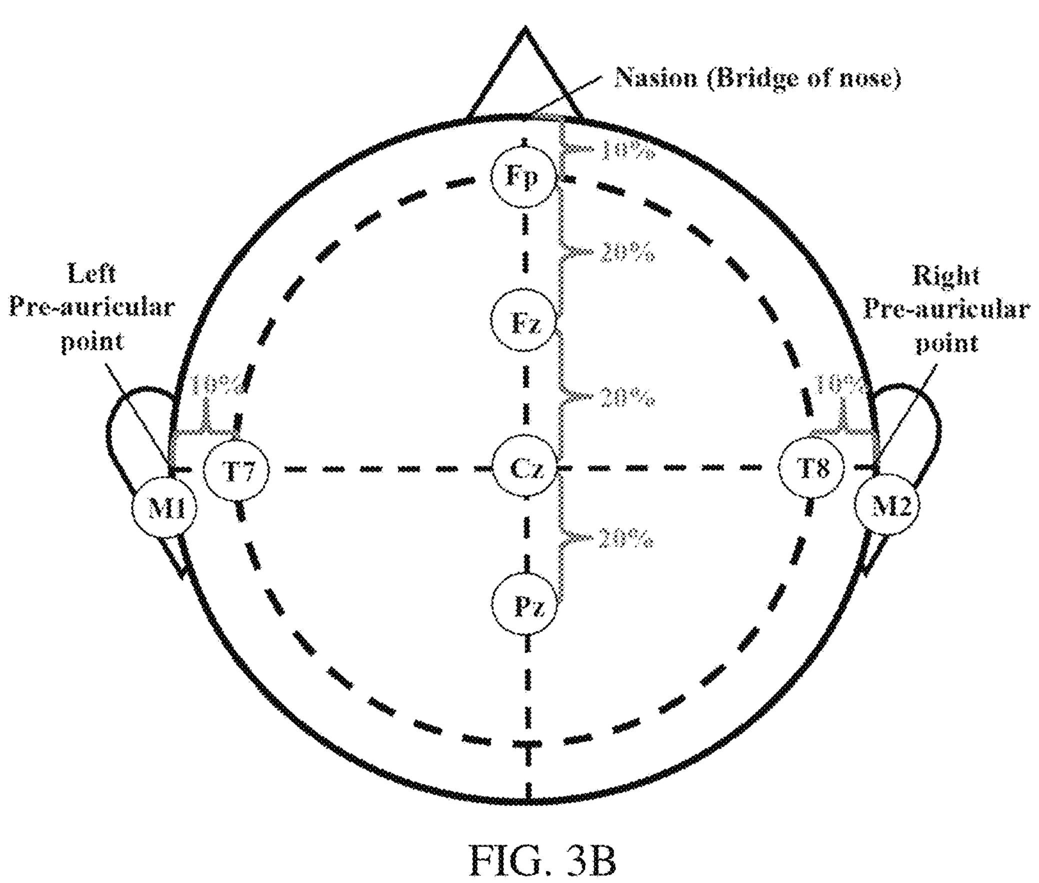
FIG. 3B illustrates EEG electrode positions in the EEG test of FIG. 3A.
Figure 3C:
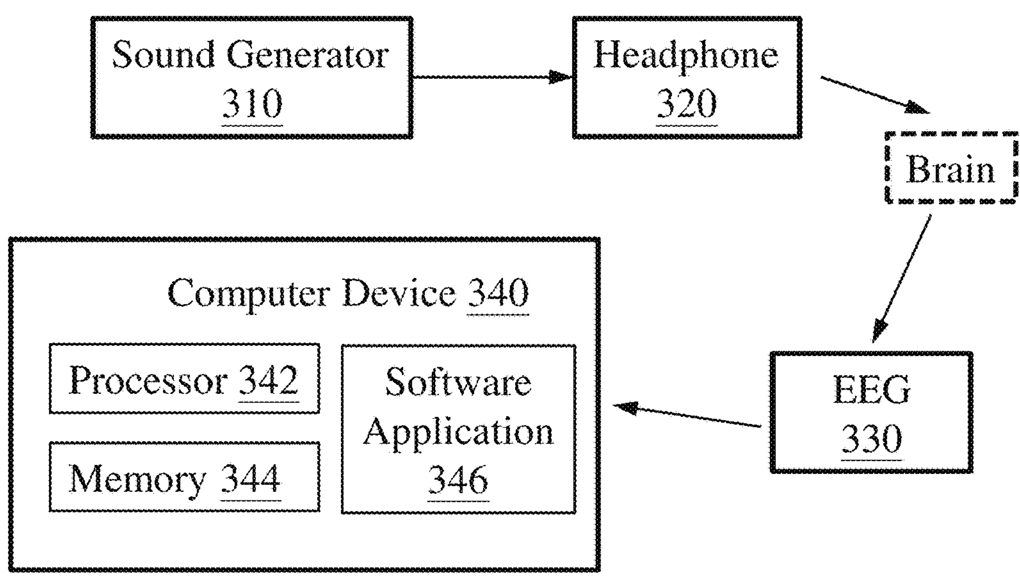
FIG. 3C illustrates an experimental setup of the EEG test of FIG. 3A.

Referring to FIGS. 3A, 3B, 3C, and 3D, to scrutinise the reliability and consistency of the acoustics perception response by the participants to the sound stimuli, the neural responses of the participants with regard to the sound stimuli are measured through an Electroencephalography (EEG) test. The experimental setup is shown in FIG. 3C. A sound generator 310 (such as a computer with a sound generating software) generates sound or acoustic signals that are inputted into a headphone 320 wearable on a participant's head. The acoustic signals stimulate the participant's brain, and the electrical activity in the brain is measured by an EEG 330 through small, metal electrodes attached to the scalp of the participant. The measured data are then inputted and processed by a computer device 340. The computer device 340 comprises a processor 342, a memory 344, and a software application 346. The software application 346, such as a MATLAB program, when executed by the processor 342, cause the processor 342 to perform one or more steps to process the measured data, as illustrated below.

In the present embodiment, the sound stimuli in this embodiment are focused on 18 soundtracks comprising the same frequencies (250 Hz, 500 Hz, 1000 Hz, 2000 Hz, 4000 Hz, and 8000 Hz) in the aural perception test described above and three different sound intensity hearing levels of 40, 60, and 78 dB HL. The quantity of acoustic stimuli in the EEG test is less than that in the acoustics perception response section because the time required cannot be too long for participants with autism to endure. All sound stimuli are generated through a Panasonic RP-HD5 headphone controlled by the E-Prime 2.0 software with a duration of 200 ms and a 20 ms onset/offset ramp. In this experiment, the participants sit in a comfortable chair in a soundproof, electrically shielded, and dimly lit chamber, as shown in FIG. 3A. During the entire experimental process, the participants are instructed not to pay attention to the sound and watch the silent movie of their choice. They are asked to remain still and try to blink less frequently. As shown in FIG. 3B, three EEG electrodes, denoted as Fz, Cz, and Pz, are placed in the frontal, central, and parietal positions, respectively, along the midline sagittal plane of the head. Another two electrodes are situated on the left and right sides of the temple of the head and are denoted as T7 and T8, respectively. The brain wave signal captured by electrodes placed on the Waveguard™ EEG cap is recorded by the ANT-Neuro Eego™ mylab amplifier. The electrode located on the left mastoid (M1) is regarded as the reference, and the frontopolar midline electrode is regarded as the ground. The electrode located on the right mastoid (M2) is recorded for re-referencing in the offline processing stage. Four additional Ag/AgCl cup electrodes are placed near the eyes to monitor the eye movement. The electrodes are fabricated from sintered Ag/AgCl by COMPUMEDICS®. The electrode impedances are maintained below 5 kΩ. The EEG is sampled at a rate of 1 kHz for the entire session. Each sound stimulus is generated 40 times in a randomised pattern for each participant. The interstimulus interval is jittered between 2 s and 3 s. The entire test consists of 720 trials and lasts approximately 55 min.

Figure 3D:
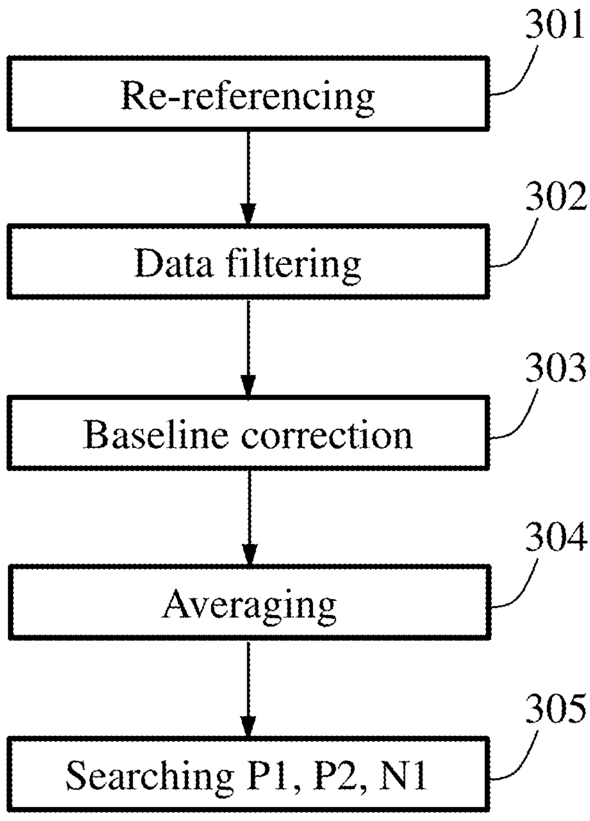
FIG. 3D illustrates how the recorded EEG data are processed according to certain embodiments of the present disclosure.

FIG. 3D illustrates one example how the computer device 340 processes the recorded EEG data (i.e. the measure data by EEG 330) that are imported into MATLAB for offline processing and analysis to investigate the relationship between the electrophysiological and aural perception responses to auditory stimuli. The EEG data are re-referenced to the averages of the left and right mastoids (Block 301). This provides a symmetrical reference that is not partial to one of the hemispheres. The equation for the referencing procedure is shown below, using channel Fz as an example. This referencing procedure is repeated for each EEG channel recorded. Let $V_{Fz}$, $V_{M1}$ and $V_{M2}$ be the absolute voltages at sites Fz, M1, and M2, respectively. Let $V_{F_z}''$ be the voltage at site Fz after the re-referencing.

$$V_{F_z}'' = V_{F_z} - \frac{1}{2}\left(V_{M_2} + V_{M_1}\right) \tag{1}$$

Block 302 states data filtering. In the present embodiment, the re-referenced data are filtered using a windowed-sinc filter as a notch filter at 50 Hz with a filter kernel length of 1650 points to remove line noise. The filter kernel is given by $h[i]=\sin(2\pi f_c i)/i\pi$. Another windowed-sinc filter with a cutoff frequency of 40 Hz and a filter kernel length of 3300 points is used as a low-pass filter to mitigate high-frequency noise such as muscle artefacts. A windowed-sinc filter with a cutoff frequency of 1 Hz and a filter kernel length of 3300 points is then utilised as a high-pass filter to minimise the low-frequency noise possibly caused by body movement, improper skin-electrode contact, and respiration. Bad channels and noisy segments are removed and corrected using an artefact subspace reconstruction approach. To investigate the electrophysiological response elicited in response to the sound stimuli, specific time windows around the onset of each sound stimulus are extracted from continuous EEG recordings. These time windows are time-locked to the sound stimuli and called epochs. In this study, the continuous EEG data are separated into 600-ms epochs with 100 ms before each stimulus onset and 500 ms after each stimulus onset. The 100-ms time intervals before each stimulus onset (baseline period) are used for realizing baseline correction (Block 303), where the mean value of the EEG data in these 100-ms pre-stimulus time intervals is computed and then subtracted from every time point of the baseline period and the post-stimulus interval for each epoch. Baseline correction is performed to reduce the effect of baseline differences between epochs that are not meaningful for interpretation and may have biased the data analysis results. Epochs with signal amplitude exceeding ±90 μV in any channel are excluded. Epochs corresponding to the same sound stimulus are averaged (Block 304) such that the spontaneous background EEG activity, such as noise, is averaged out, leaving the time-locked EEG response elicited by the sound stimulus distinct from the background. This averaging procedure is repeated for each sound stimulus, and the resulting time-locked EEG responses are exported. To ensure reliability of the results, only data with components in the period described by traditional slow-wave cortical auditory evoked potentials are included in the analysis. These components are characteristic deflections that occur around specific peak latencies, where the peak latency is measured using the stimulus onset as the reference point (i.e., 0 ms begins at stimulus onset). In this study, the first and second positive peaks are denoted as P1 and P2, with peak latencies of approximately 50 ms and in the 175-200 ms range, respectively. The first trough point, denoted as N1, is a prominent negative wave peaking at approximately 100 ms. The peak amplitudes and latencies of the P1, N1, and P2 components in the temporal signals of event-related electrical potentials are used to quantify neural responses of the participants toward the auditory stimuli. These response characteristics are substantially influenced by physical attributes of the provocation, such as the duration of sound stimuli, rise time (time taken by the sound signal from silence to peak amplitude), sound intensity level, interstimulus interval, and stimulus features. At Block 305, to identify these three components, searching is focused for the peaks of P1 and P2 in the periods 20-120 ms and 150-250 ms, respectively. For the first trough point, the N1 component, the search window is focused from 70 ms to 150 ms. In the analysis, a peak is identified as the data point with the maximum positive amplitude for P1 and P2 and the data point with the maximum negative amplitude for N1 within the search window. The peak amplitude value is measured as the average magnitude of data±1 ms around the peak, which is the average value of the peak and the values of data 1 ms before and after the peak. The peak amplitudes and latencies of the P1, N1, and P2 components are investigated.

To enhance the quality of data, participants are included in the analysis only if they display consistent and reliable responses in both the aural perception and EEG tests. In the aural perception test, the consistency of the participants across three repeated assessments of the aural perception test is evaluated using the one-way random effects, absolute agreement, multiple measurements intraclass correlation coefficient (ICC). A score less than or equal to 0.38 is regarded as inconsistent and excluded from the data analysis. In addition, participants who have fewer than 540 epochs after data pre-processing and cleaning are excluded. Consequently, 33 ASD and 12 TD participants are excluded. In total, 50 ASD and 38 TD participants aged 7-12 years are included in the analysis.

The score of the aural perception test response are adjusted to a positive number from (−2 to +2) to (1 to 5), wherein the adjusted scale rating 1 represents "strongly dislike" and rating 5 represents "strongly like". This scale adjustment is performed for ease of data analysis and interpretation of aural perception and electrophysiological responses to sound stimuli. For each participant, the responses to each sound stimulus across three repeated assessments in the aural perception test are averaged to obtain a mean score. This results in 36 mean scores for each participant. These scores represent the individual variation patterns of each participant and are adopted for further analysis below. In addition, the mean scores for all 36 sound stimuli are added to the total score for each participant. The total score measures the aural perception of the participants, while considering their responses to 36 sound stimuli with a uniform weighting. A lower total score indicates a greater dislike toward the sound stimuli, while a higher total score indicates a greater liking for the sound stimuli. The total scores of all the TD participants are averaged to obtain a mean total score and used as the cutoff for categorisation into two groups of participants with autism. Those with a total score higher than the TD cutoff are classified as ASD group 1, whereas those with a total score less than the TD cutoff are classified as ASD group 2.

Figure 4:
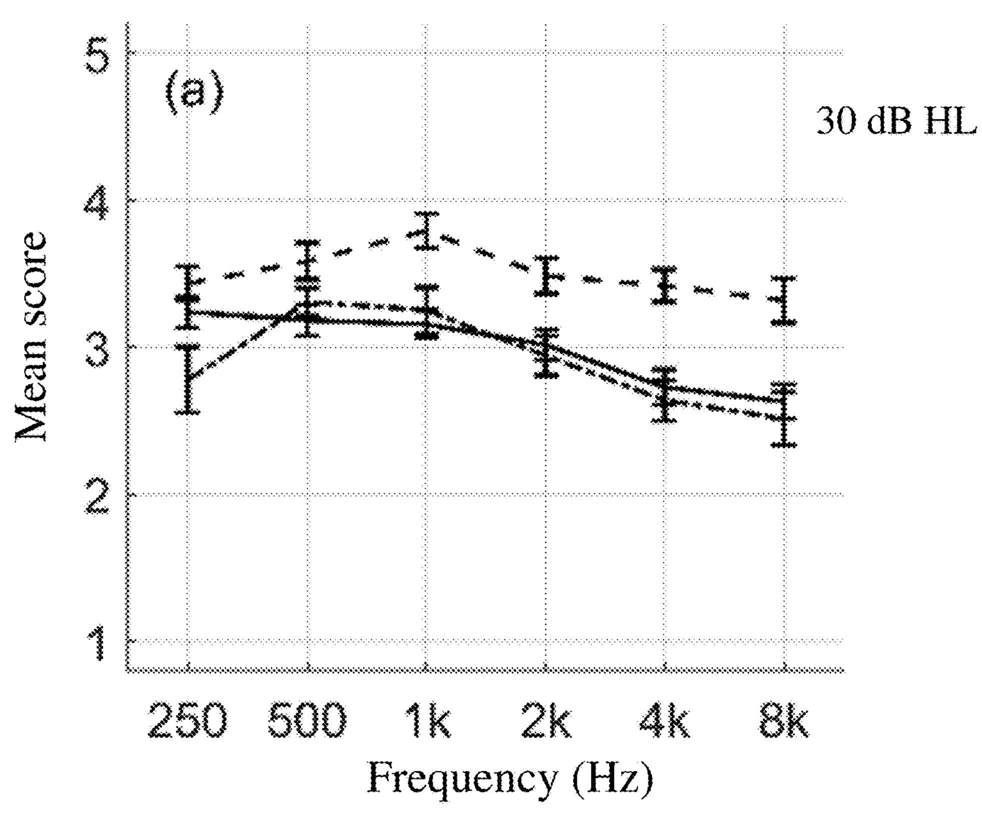
FIG. 4 illustrates aural perception mean scores with grouping at different sound intensity hearing levels: (a) 30 dB HL; (b) 40 dB HL; (c) 50 dB HL; (d) 60 dB HL; (e) 70 dB HL; (f) 78 dB HL.
Figure 4:
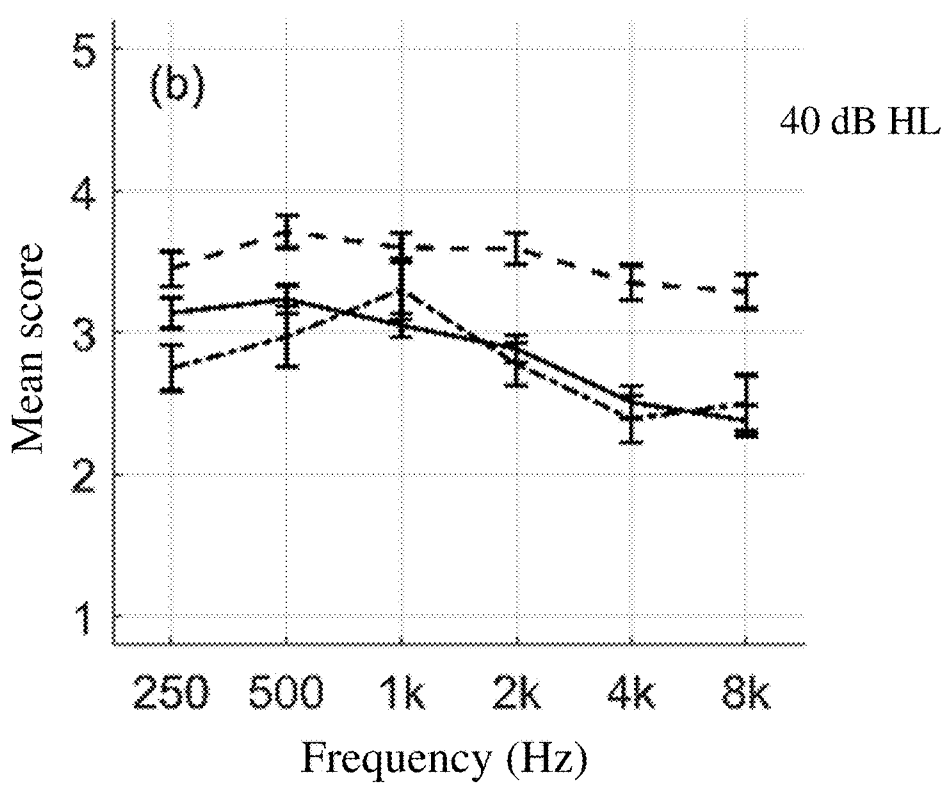
Figure 4:
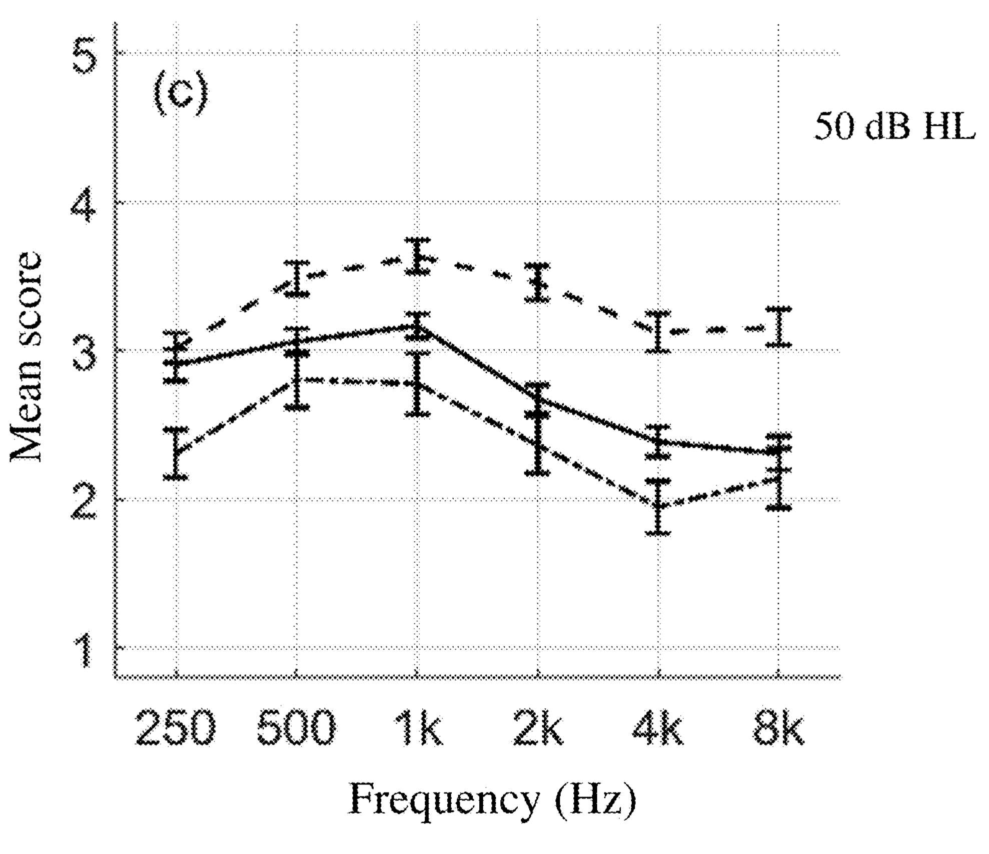
Figure 4:
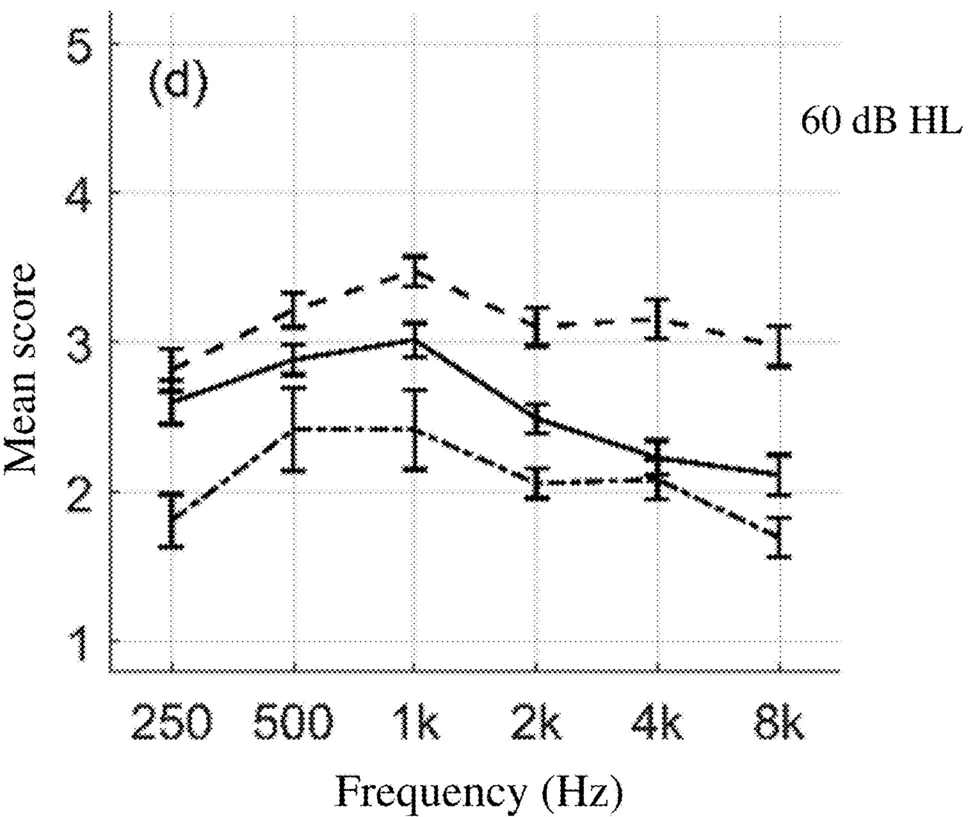
Figure 4:
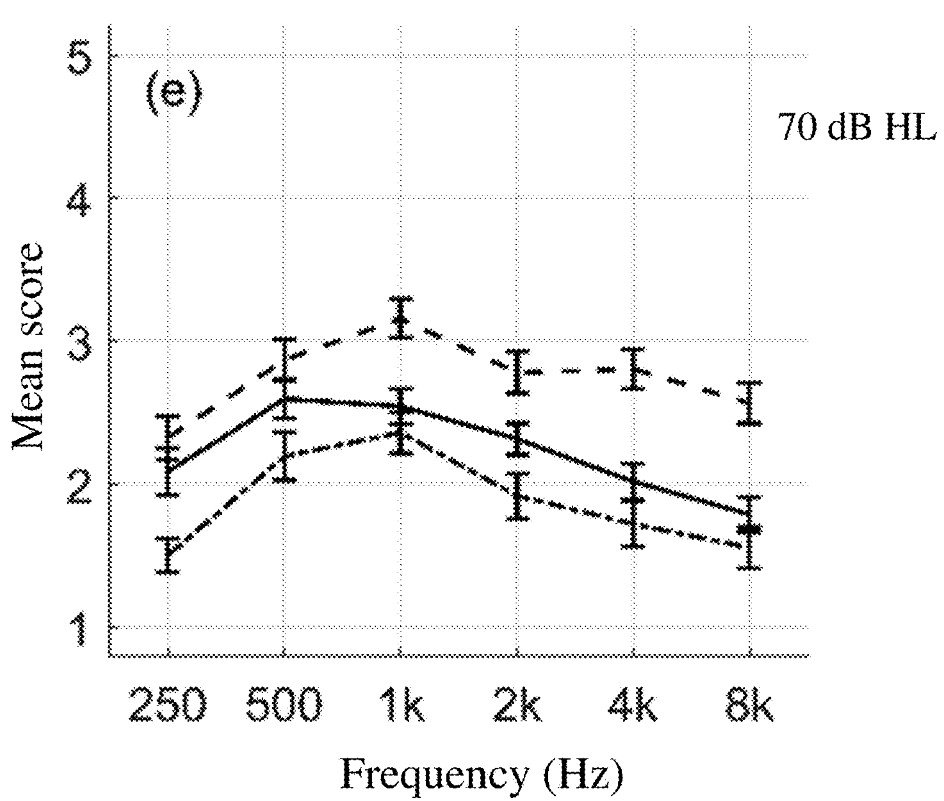
Figure 4:
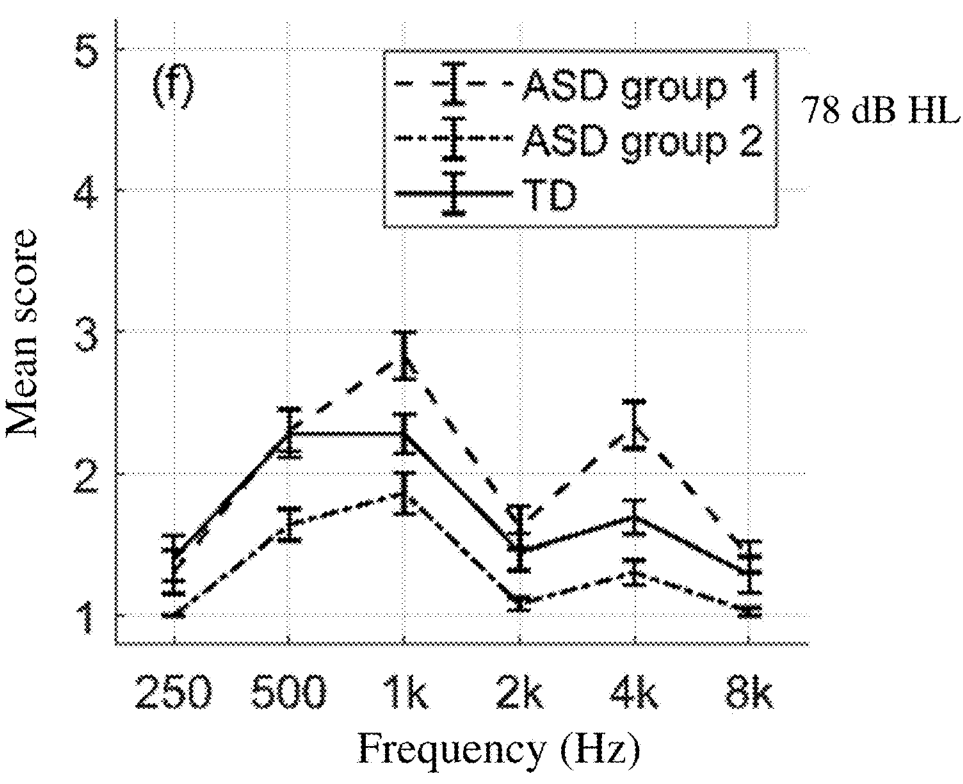

The mean scores of the two ASD groups and the TD group based on the aural perception experiment are presented in FIG. 4. As can be seen, the mean score of the ASD group 1 (as indicated by dashed lines) is higher than that of TD at all the frequencies and sound intensity hearing levels, except at 250 Hz at 78 dB HL. At lower sound intensity hearing levels, such as 30 and 40 dB HL, the mean score increases in the frequency range of 250 Hz to 1 kHz, then decreases toward the frequency of 8 kHz. This indicates that they dislike frequencies at 250 Hz and 8 kHz more and are generally willing to listen to sounds in the mid-range frequency of approximately 1 kHz. At 50 dB HL and 60 dB HL, the differences between the mean scores at 250 Hz and 8 kHz versus those at other frequencies become more noticeable. At 70 dB HL, the profile of the mean score variation against frequency is similar to that at 50 and 60 dB HL, and the mean score at almost all the frequencies is lower than 3, which indicates that they dislike these sounds. The mean score curve of ASD group 1 is notably higher for the majority of the presented sound stimuli than for the TD participants. This result indicates that ASD group 1 had a higher tolerance to high-intensity sounds. ASD group 2 (as indicated by dash-dotted lines) has a relatively lower mean score for all the sound stimuli compared to the TD group, but manifests a similar variation pattern to the TD group. At 30 and 40 dB HL, the responses resemble the TD responses, except for a substantially lower mean score at a frequency of 250 Hz. At 50-70 dB HL, this group of participants with autism exhibits an unpleasant response to all the sound stimuli, and a lower mean score is observed at all frequencies compared with the TD group.

The results from above show that the majority of participants with autism dislike very low and very high frequencies. To validate the subjective aural perception, the relationship between this response and the EEG results is investigated. Spearman's correlation analysis is used to analyse their correlations. The results of ASD participants combining groups 1 and 2 and those of TD participants are listed in Table 1 below. In the ASD group, there are significant correlations between aural perception and absolute N1 peak amplitude and P1 and P2 peak latencies at specific EEG channels. The correlation coefficients for N1 peak amplitude ranged from −0.118 to −0.149, $p<0.01$, and for P1 and P2 peak latencies, coefficients range from 0.122 to 0.194, $p<0.01$. In the TD group, significant correlations are found between aural perception and absolute N1 peak amplitude and P1 and P2 peak latencies across multiple EEG channels, with correlation coefficients ranging from −0.103 to −0.270, $p<0.01$ and 0.109 to 0.170, $p<0.01$, respectively. Aural perception is a subjective evaluation of the sound provided by participants, whereas the neural response displays an objective reaction to sound. The correlation between these two responses suggests that the mean aural perception score is indicative of the participants' subjective perception of the presented sound stimuli. For both the ASD and TD groups, the absolute N1 peak amplitude generally exhibits a better association with the aural perception response. This indicates that the N1 peak amplitude may be a suitable candidate for quantifying participant's neural responses to sound stimuli. In general, the higher the sound intensity hearing level, the higher the absolute peak amplitude of the components N1 and lower is the peak latency.

TABLE 1

Spearman correlation between event related potential (ERP) component response and ratings in aural perception test

| | Parameters | Fz | T7 | Cz | T8 | Pz |
|---|---|---|---|---|---|---|
| ASD | Absolute P1 peak amplitude and rating | −0.047 | 0.060 | 0.001 | −0.030 | 0.016 |
| | Absolute N1 peak amplitude and rating | −0.099** | −0.133** | −0.125** | −0.149** | −0.118** |
| | Absolute P2 peak amplitude and rating | 0.005 | 0.099** | −0.054 | 0.055 | −0.043 |

TABLE 1-continued

Spearman correlation between event related potential (ERP) component response and ratings in aural perception test

| | Parameters | Fz | T7 | Cz | T8 | Pz |
|---|---|---|---|---|---|---|
| | P1 peak latency and rating | 0.132** | 0.048 | 0.148** | 0.086* | 0.122** |
| | N1 peak latency and rating | 0.024 | 0.077* | 0.107** | 0.074* | 0.108** |
| | P2 peak latency and rating | 0.135** | 0.030 | 0.194** | 0.003 | 0.179** |
| TD | Absolute P1 peak amplitude and rating | 0.043 | −0.032 | 0.020 | −0.065 | 0.005 |
| | Absolute N1 peak amplitude and rating | −0.103** | −0.230** | −0.161** | −0.270** | −0.165** |
| | Absolute P2 peak amplitude and rating | 0.037 | 0.018 | −0.096* | 0.000 | −0.117** |
| | P1 peak latency and rating | 0.170** | 0.109** | 0.136** | 0.057 | 0.151** |
| | N1 peak latency and rating | 0.059 | 0.087* | 0.100** | 0.094* | 0.098* |
| | P2 peak latency and rating | −0.018 | 0.091* | 0.076* | 0.020 | 0.072 |

*Correlation is significant at the 0.05 level (2-tailed).

**Correlation is significant at the 0.01 level (2-tailed).

Figure 5:
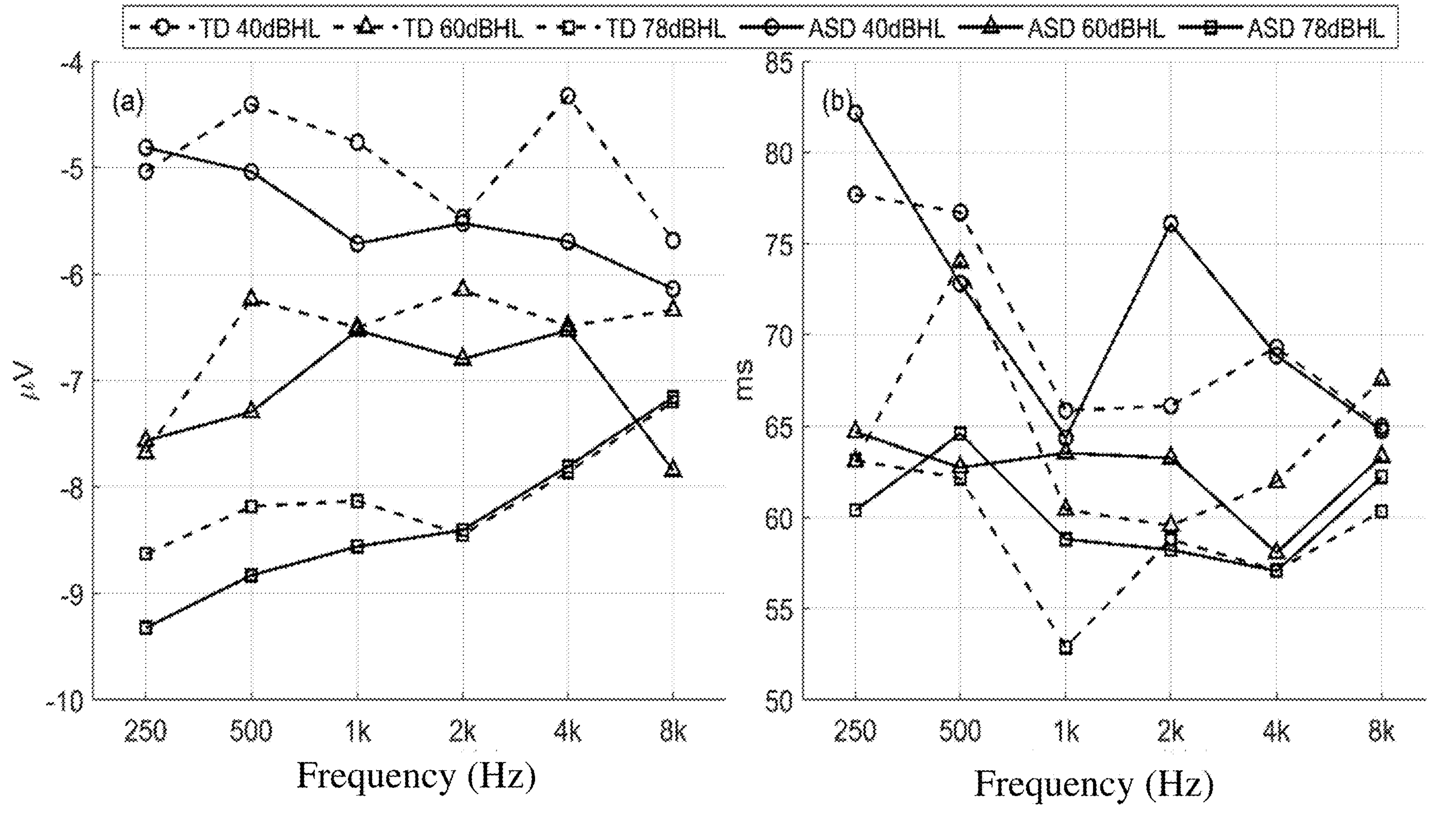
FIG. 5 illustrates comparison of (a) peak amplitude and (b) peak latency of N1 components at channel T8 of typical growth (TD) and ASD groups.

FIG. 5 illustrates a comparison of the peak amplitude and peak latency N1 components at channel T8 in the TD and ASD groups. Channel T8 is selected because relatively high correlation coefficient values are observed in this channel in both the ASD and TD groups. The results of the TD participants provide a baseline for how the frequency and sound intensity hearing levels would affect the peak amplitude and peak latency of the components. In general, the higher the sound intensity hearing level is, the higher the absolute peak amplitude of the components will be. In addition, the higher the sound intensity hearing level is, the lower the peak latency will be. This is clearly observed in the N1 component. When looking at the N1 peak amplitude, the TD group has an overall smaller magnitude than the ASD group.

Participants with autism may have distinct acoustic responses and individual acoustic sensitivities to different types of sound sources. Some participants may like a particular type of sound, but others may find it unpleasant. This suggests that the physical properties of sounds that provoke problematic behaviour vary from person to person. Therefore, a headset with the same noise-control strategy and algorithm is inappropriate for participants with different aural perception responses and sensations. Therefore, it is essential to provide customised noise control for autistic participants with different frequency profiles. To achieve this, a clustering analysis is conducted to cluster participants with autism into different subgroups based on their aural perception, and each group will have a similar frequency profile.

Clustering algorithms include prototype-based clustering and hierarchical clustering, which vary on the nature of grouping mechanism. One of the methods under prototype-based clustering is K-means clustering which can be adopted as partition algorithm. It is a method of vector quantization that is used to partition certain number of participants into K clusters in which each participant belongs to the cluster with the nearest mean value or centroid. This method requires the number of clusters (K), cluster initialization and the distance metric as input parameters. Let $X=\{x_i\}$, $i=1, \ldots n$ be the dataset to be clustered into a set of K clusters where $x_i$ is a vector of mean aural perception scores of the ith ASD participants and n is the total number of ASD participants adopted in the analysis. Let $C=\{c_k\}$ be the set of clusters, $k=1, \ldots, K$ be the number of clusters to be formed and $\mu_k$ be the mean of cluster $c_k$. The squared error between $\mu_k$ and the points in cluster $c_k$ is defined as $$J(c_k) = \sum_{x_i \in c_k} \|x_i - \mu_k\|^2 \tag{2}$$

Figure 6:
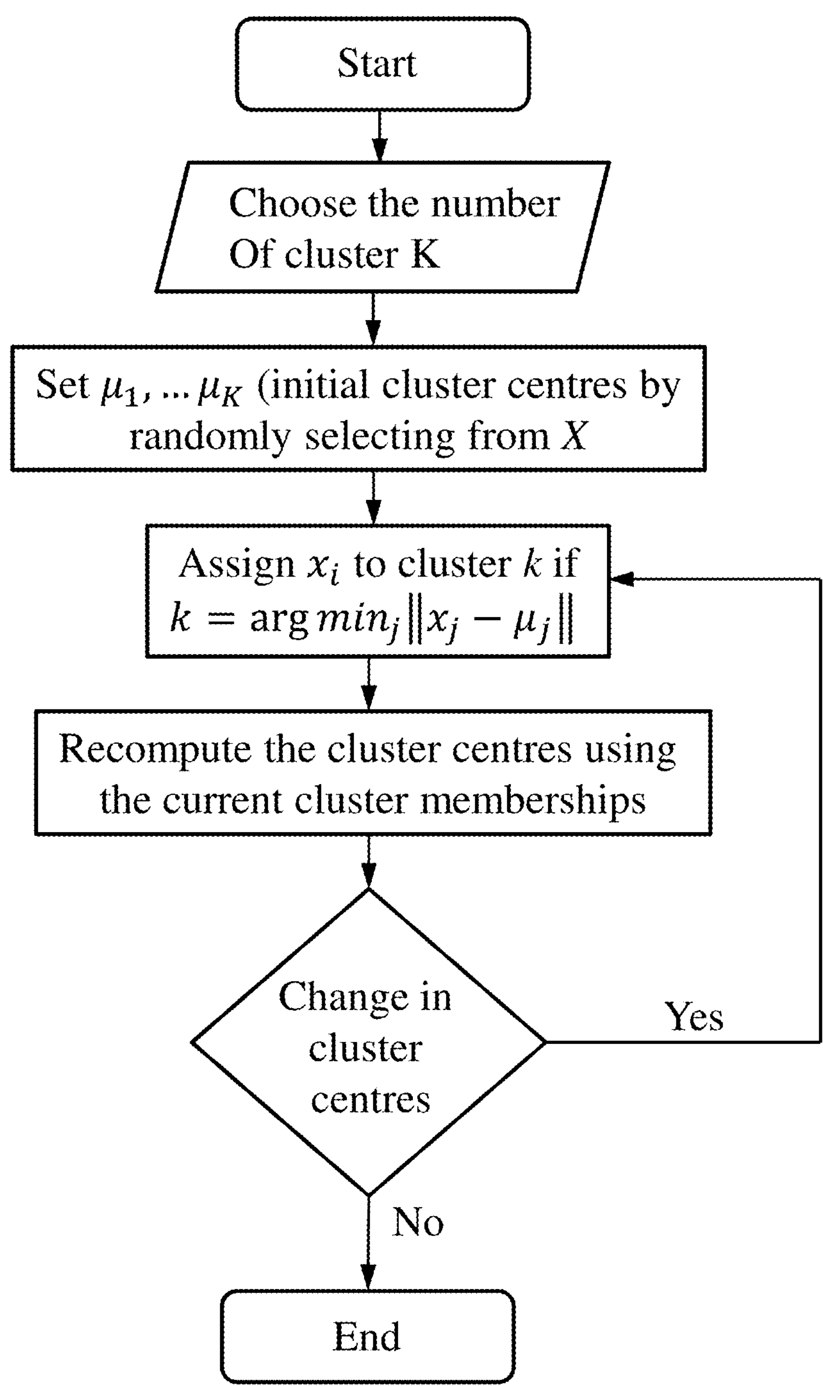
FIG. 6 illustrates a K-means clustering algorithm block diagram according to certain embodiments of the present disclosure.

The goal of k-means is to minimize the sum of squared error (SSE) over all K clusters, $$J(c_k) = \sum_{k=1}^{K} \sum_{x_i \in c_k} \|x_i - \mu_k\|^2 \tag{3}$$

and finds a partition such that the squared error between the empirical mean of a cluster and the data points in the cluster is minimized. After the parameter K is decided, the k-means algorithm begins by initializing K randomly selected vector of mean aural perception scores in the dataset as the initial cluster centres ($\mu_k$). For each ASD participant, the Euclidean distance between the vector of mean aural perception scores and all cluster centres are calculated. The ASD participant is assigned to the cluster with the smallest Euclidean distance. When all ASD participants are assigned to a cluster, the cluster centres are recomputed using the current cluster memberships. Then, the process of calculating the Euclidean distance between the ASD participants and cluster centres are repeated until there are no changes in cluster assignment for all ASD participants. The block diagram of K-means clustering algorithm is shown in FIG. 6.

Among the input parameters, the most critical parameter is the number of clusters K. Currently, there is no perfect mathematical criterion for determining K. A typical heuristic for selecting K is to run the algorithm independently for different values of K and select a partition that appears to be the most meaningful solution to the problem. This approach is adopted in the current study, and the method used to select K is based on cluster validation indices.

Another input is the cluster initialisation. As K-means converges only to local minima, different initialisations can result in different clustering solutions. To overcome this problem, each number of clusters is initialised using 10,000 different initial centroid positions. This number of initialisations is selected because it provides a stable cluster solution and membership assignment in the current cluster analysis across different values of K. Subsequently, the partition with the smallest sum of squared errors is selected.

Another approach for analysing the current data is the use of agglomerative hierarchical algorithms (HCAs). This analysis involves building a hierarchy of clusters using the "bottom-up" approach. It begins with each data point as a separate cluster and merges them into successively larger clusters until all the data are grouped into one large cluster. At each clustering step, the clusters having the smallest distance are joined together, and there are multiple methods of determining the distance between two clusters, which is referred to as a linkage. Several indicators can be used to examine or determine how to combine or split the clusters. For example, an average linkage measures the cluster distance as the average of all pairwise distances between data points in two clusters and Ward's linkage, which is based on the Euclidean distance between two cluster centroids multiplied by a factor. The closest pair of clusters computed using this method results in the smallest increase in the total SSE of the dataset. On comparing these linkage methods, Ward's linkage and the average linkage are generally more effective in capturing the clustering structure than the single linkage and complete linkage. Therefore, the average linkage and Ward's linkage are used in the agglomerative hierarchical clustering algorithm. The silhouette index, Calinski-Harabasz index, and Davies-Bouldin index are used in this study to select the appropriate clustering algorithm and optimal number of clusters because they are demonstrated to be some of the best-performing cluster validation indices in both artificial and real datasets. These three indices provided better results, even in datasets with often problematic features such as high dimensionality, density asymmetry, and cluster overlap, which might also be present in our dataset.

Figure 7:
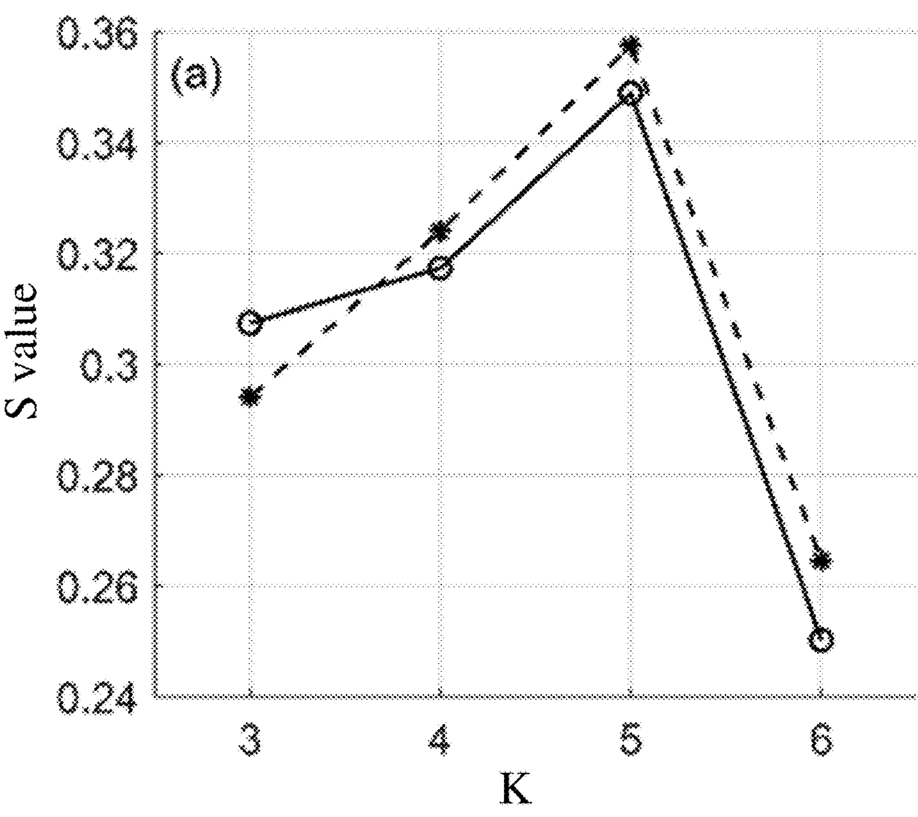
FIG. 7 illustrates results of cluster validation indices with the three clustering methods with K of 3-6: (a) Silhouette index; (b) Calinski-Harabasz index; (c) Davies-Bouldin index according to certain embodiments of the present disclosure.
Figure 7:
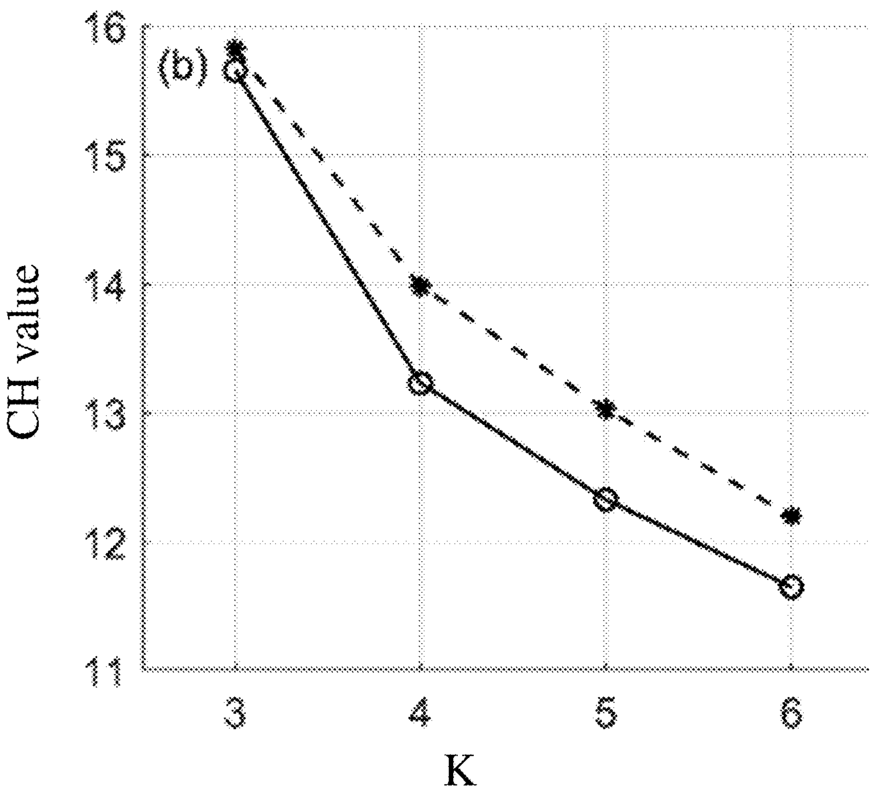
Figure 7:
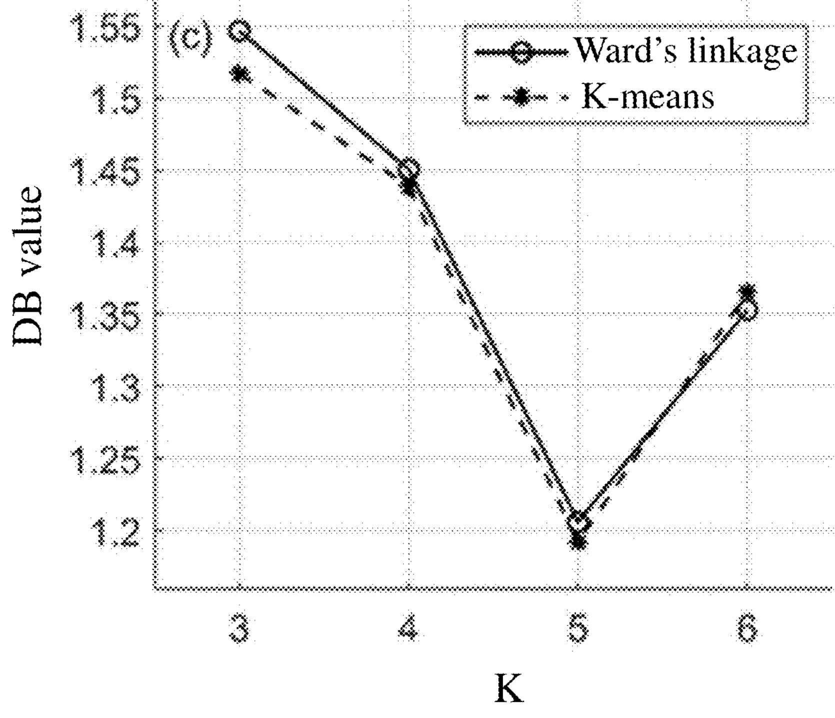

A comparison of the clustering results of the three methods is presented in Table 2 below, which displays the cluster membership assignments of the selected K. Clustering methods are distributed in rows, whereas individual clusters are distributed in columns. Among the three clustering methods, only the HCA-average linkage tends to form a large cluster that includes the majority of the participants and a few small clusters that include one to four members, regardless of the value of K. Because the aim of performing clustering is to group participants with similar frequency profiles, the cluster solution should not comprise a single cluster that includes almost all the participants, especially those with the heterogeneous aural perception responses. Thus, this solution is unsuitable for the current purposes. For the other two algorithms, the partitions are of similar size. The results of the cluster validation indices are presented in FIG. 7. In the case of the silhouette and Calinski-Harabasz indices, a better partition is indicated by a higher value, while in that of the Davies-Bouldin index, a lower value indicates a better partition. As suggested by the cluster validation indices, the K-means algorithm exhibits a slightly better performance than the HCA-Ward's linkage, and thus, the cluster solution of the former is selected. For the number of clusters to be formed, K=5 is suggested by two of the three cluster validation indices as the best cluster assignment. Therefore, the ASD group is split into five clusters based on the results of the K-means clustering algorithm.

TABLE 2

Cluster membership assignments from the clustering algorithms: K-Means, HCA-Average linkage, and HCA-Ward's linkage; K = 3 to 6

| K = 3 | Cluster 1 | Cluster 2 | Cluster 3 |
|---|---|---|---|
| K-Means | 30 | 15 | 5 |
| HCA-Average linkage | 1 | 4 | 45 |
| HCA-Ward's linkage | 15 | 30 | 5 |

TABLE 2-continued

Cluster membership assignments from the clustering algorithms: K-Means, HCA-Average linkage, and HCA-Ward's linkage; K = 3 to 6

| K = 4 | Cluster 1 | Cluster 2 | Cluster 3 | Cluster 4 |
|---|---|---|---|---|
| K-Means | 6 | 5 | 23 | 16 |
| HCA-Average linkage | 1 | 3 | 1 | 45 |
| HCA-Ward's linkage | 4 | 26 | 15 | 5 |

| K = 5 | Cluster 1 | Cluster 2 | Cluster 3 | Cluster 4 | Cluster 5 |
|---|---|---|---|---|---|
| K-Means | 16 | 23 | 1 | 6 | 4 |
| HCA-Average linkage | 1 | 44 | 1 | 3 | 1 |
| HCA-Ward's linkage | 1 | 4 | 4 | 26 | 15 |

| K = 6 | Cluster 1 | Cluster 2 | Cluster 3 | Cluster 4 | Cluster 5 | Cluster 6 |
|---|---|---|---|---|---|---|
| K-Means | 6 | 18 | 7 | 14 | 4 | 4 |
| HCA-Average linkage | 4 | 40 | 1 | 1 | 3 | 1 |
| HCA-Ward's linkage | 6 | 20 | 1 | 4 | 4 | 15 |

Figure 8:
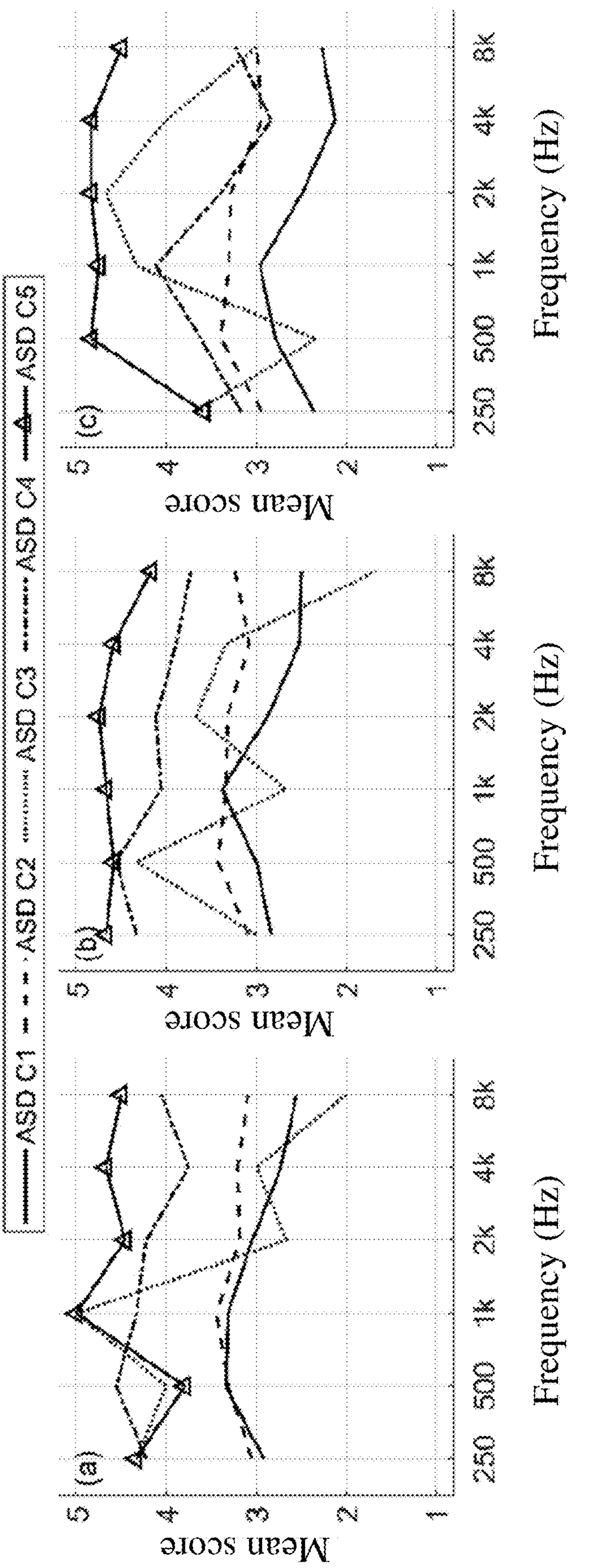
FIG. 8 illustrates aural perception mean scores of the five clusters from K-means algorithm at different sound intensity hearing levels: (a) 30 dB HL; (b) 40 dB HL; (c) 50 dB HL; (d) 60 dB HL; (e) 70 dB HL; (f) 78 dB HL.
Figure 8:
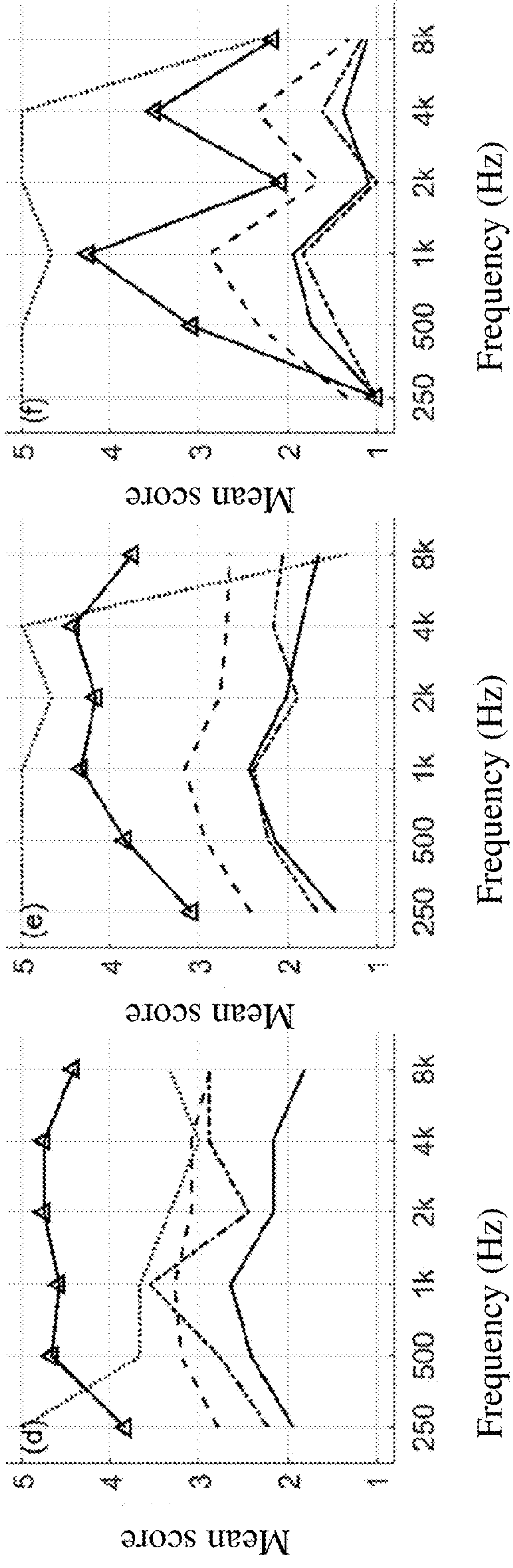

Based on the K-means clustering approach, the characteristics of the clustered group of participants with autism with corresponding frequency profiles at different dB HL are investigated. FIG. 8 shows that the first cluster (ASD C1) rates frequencies of 4 kHz and 8 kHz as unpleasant at low sound intensity levels, while frequencies of 250 Hz, 500 Hz, and 2 kHz are rated as neutral, and 1 kHz is rated as like. At higher sound intensity levels, all frequencies are rated as unpleasant, with 250 Hz, 4 kHz, and 8 kHz being the most unpleasant. The second cluster (ASD C2) rates frequencies as neutral or similar at low sound intensity levels, and rates 250 Hz and 8 kHz as unpleasant at 60 dB HL, 2 kHz and 4 kHz as unpleasant at 70 dB HL, and all frequencies as dislike at the highest sound intensity level. The third cluster (ASD C3) rates all sounds above a score of 2 (dislike), except for 8 kHz at certain sound intensity levels. The fourth cluster (ASD C4) rates frequencies as neutral or like at low sound intensity levels, and rates 250 Hz, 500 Hz, and 2 kHz as unpleasant at 60 dB HL, and all frequencies as dislike at higher sound intensity levels. The fifth cluster (ASD C5) rates most frequencies as like, with 250 Hz being the only frequency rated as dislike at higher sound intensity levels.

For all the clusters, the frequencies that trigger the most unpleasant feeling at a higher sound intensity hearing level are 250 Hz and 8 kHz, followed by the frequency of 2 kHz as the second most unpleasant one. At the other sound intensity hearing levels, the aural perception responses from the different groups have their own characteristics. This supports the need for customised noise control that addresses the specific annoying frequencies for each group. In addition, the magnitude of noise reduction that could result in a neutral rating for the perceived sound at the presented frequencies differs from group to group, with some requiring a more drastic reduction and others preferring a moderate level. Therefore, it is vital to consider these varied responses when designing noise-control methods for autistic participants.

Figure 9A:
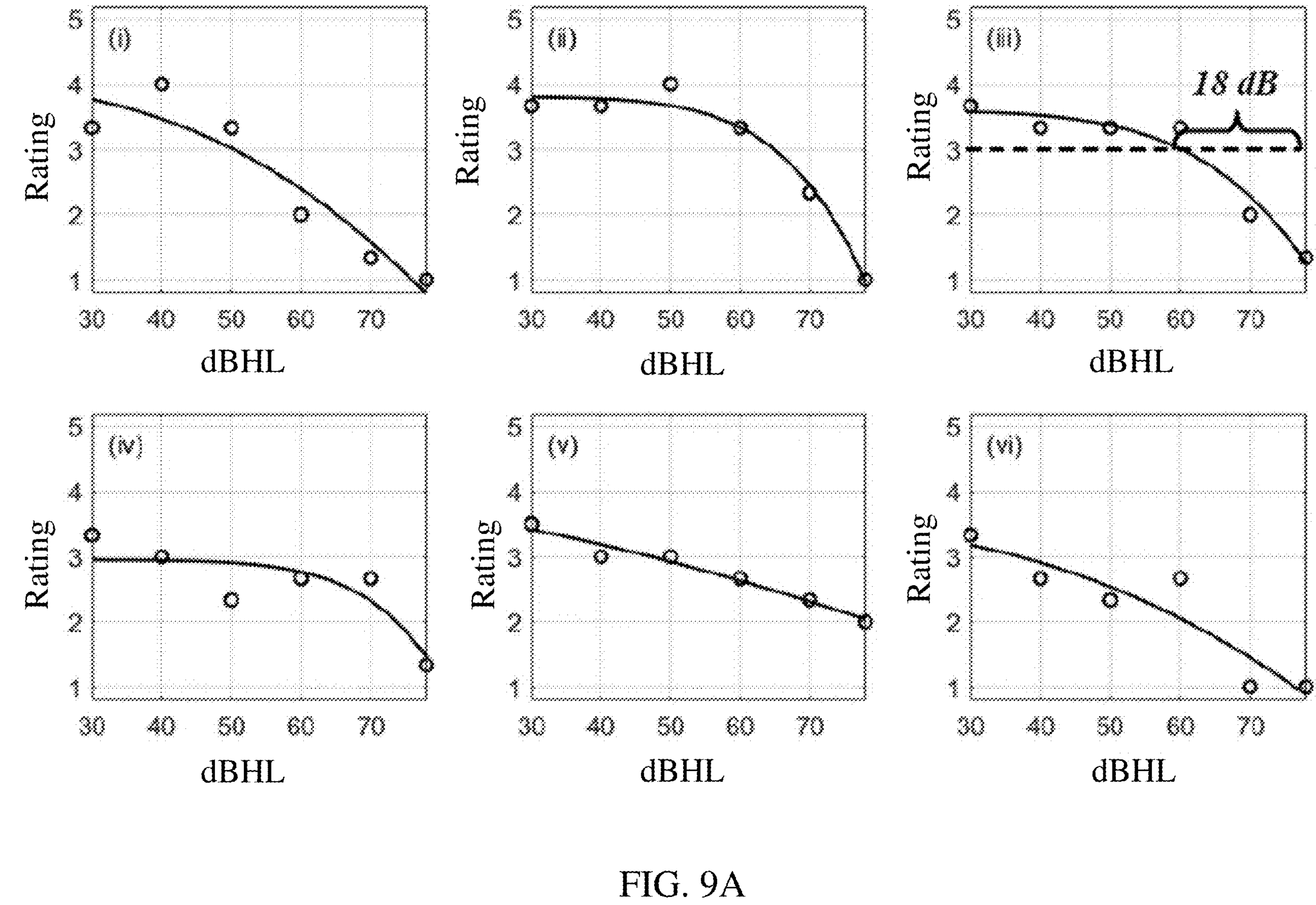
FIG. 9A illustrates hearing perception curves accompanied by aural perception responses at different frequencies: (i) 250 Hz; (ii) 500 Hz; (iii) 1 kHz; (iv) 2 kHz; (v) 4 kHz; (vi) 8 kHz.
Figure 9B:
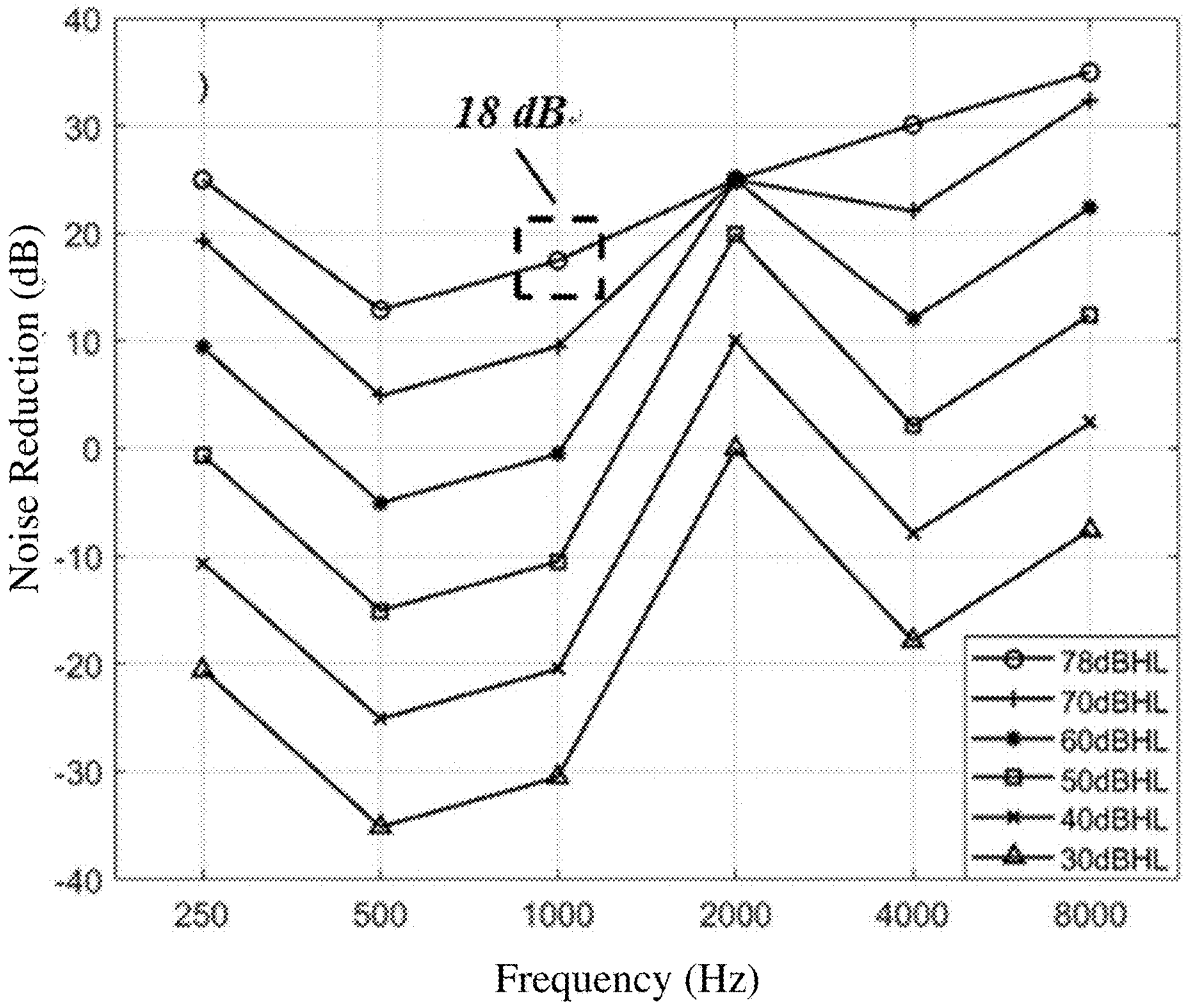
FIG. 9B illustrates resulting target curves for noise cancellation derived from FIG. 9A.

To provide noise control specified for the heterogeneous needs of autistic participants, the hearing perception curve for each corresponding subgroup is plotted based on the findings above. As the ASD group has aural perception response profiles that are different from those of the TD group, the noise control strategy is focused on providing a suitable noise control algorithm to cancel the incoming noise such that the ASD participants will have a neutral response to the resultant sound. FIG. 9A presents the aural perception ratings against the dB HL at different frequencies. To achieve a neutral response (e.g. the dashed line in FIG. 9A, subplot (iii)) as a criterion, the level of noise reduction required at each frequency is investigated. In this regard, a power function curve fitting with the mean aural perception rating and sound intensity hearing level as variables is performed. The fitted curve is used to estimate the mean aural perception rating between the sound intensity hearing levels tested at each frequency in the aural perception test. The power function is in the form of $$y_i = a(x_i^b) + c,$$

where $y_i$ is the ith mean perception rating in a specific frequency, $x_i$ is the ith intensity level in a specific frequency, and a, b, c are the coefficients to be determined. The best-fitting curve is determined using the nonlinear least-squares method by selecting the best fit with the least sum of square errors. The power function is selected because the aural perception rating is inversely proportional to the presented sound intensity hearing level. As the sound intensity hearing level increases, the change in the aural perception rating generally will decrease. Using the hearing perception curve, it is possible to estimate the noise attenuation required to induce a neutral feeling at individual frequencies, given the noise level presented to the participant. As illustrated in FIG. 9A, subplot (iii), to calculate the required noise reduction at a specific frequency, the sound intensity hearing level that presents a neutral feeling is first determined using the hearing perception curve (60 dB HL). The required noise attenuation level is given by the difference between the sound intensity hearing level and the noise level (78 dB HL-60 dB HL=18 dB HL). This provides the target curve at octave frequencies ranging from 250 to 8000 Hz for the tuning noise cancellation that is catered to hearing perception in participants with autism. FIGS. 9A and 9B illustrate the hearing perception curve along with the aural perception ratings and the resulting target curves for noise cancellation.

Figure 10A:
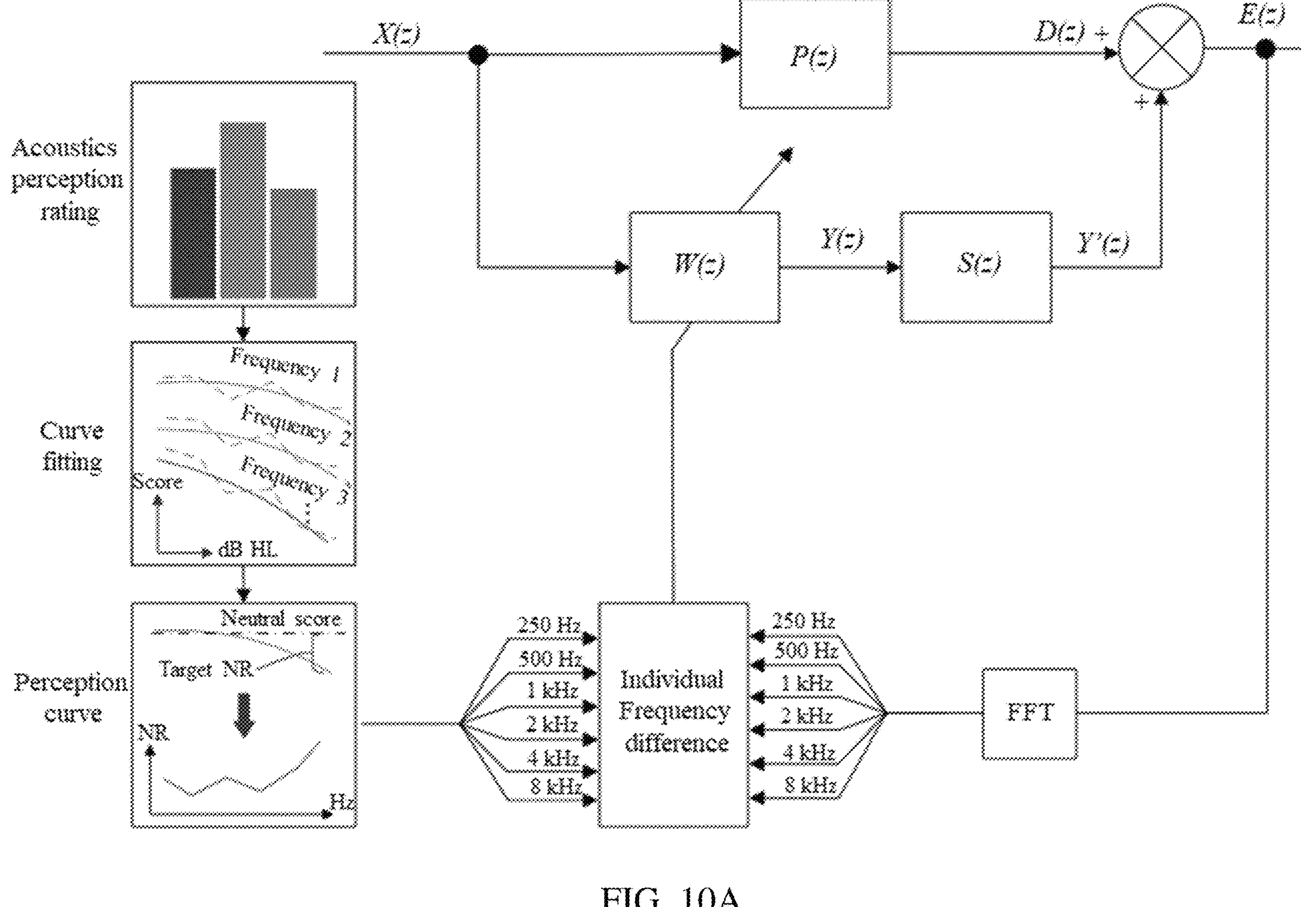
FIG. 10A illustrates a block diagram of the proposed active noise cancellation (ANC) system according to certain embodiments of the present disclosure.

Noise-cancelling headphones are commonly used by participants with autism and auditory hyperreactivity to reduce their exposure to noise and its negative effects. Commercially available noise-cancelling headphones allow users to alter the overall noise-cancelling function by adjusting the level of noise cancellation applied by the headphones. This allows users to vary the overall sound pressure level reduction. Till date, there is no designing of any noise-control strategy based on the human perception response curve, where the human perception response curve is a function of the acoustic magnitude and frequency. The present inventors have demonstrated that frequency is also a component that substantially affects the aural perception of autistic participants with auditory hyperreactivity. Thus, the ability to tune the frequency response of the noise-cancelling function, in addition to intensity, will be more beneficial to serve the purpose. To develop an ANC algorithm to ease aversive behaviours related to auditory hyperreactivity in participants with autism, the frequency response and level of noise cancellation are tuned based on the results of the aural perception test. The objective of the ANC algorithm is to achieve noise cancellation such that participants with autism can perceive incoming noise with a neutral feeling, thus minimising the effect of incoming disturbing noise on their behaviours. A block diagram of the ANC system with the proposed function is presented in FIGS. 10A and 10B. The acoustic signal comprises incoming noise. The acoustic signal can be considered as the primary signal X(z) and is measured using the reference microphone 1022 of the headphone 1020. This acoustic signal travels along the primary path P(z) (indicated by 1002 in FIG. 10B) from the exterior of the earcup into its interior. The residual signal D(z) represents the signal that remains after certain portion of the acoustic signal is absorbed by the ear cushion. The computer device 1040 outputs a cancellation signal Y(z) that travels through the secondary path (S(z))(indicated by 1004 in FIG. 10B), which includes the electronic software and hardware components, as well as the acoustic path from the loudspeaker to the error microphone 1024. Y'(z) represents the cancellation signal after travelling the secondary path S(z). It combines the residual signal D(z) and results in the cancellation of the noises based on the principle of superposition, thereby generating an error signal E(z). The adaptive noise control systems may include feedback, feedforward, or hybrid control. In feedback control, the cancellation signal is produced using the error microphone signal because feedback and reference signals are not required. However, its active-attenuation performance is limited by the resonant behaviour of the earcup cavity, which forces low feedback gains. In general, feedforward control can result in better performance than feedback control if a good reference signal is available and the system is efficient in satisfying causality. However it may suffer from stability or performance deficiencies caused by limited tolerance to gain error. The hybrid control system maintains the advantages of the feedforward and feedback control systems, overcomes the instability of the feedback system, and compensates for the poor adaptability of the feedforward system to primary noise. Therefore, a hybrid system is used in this study. The objective of the adaptive filter W(z) (indicated by 1030 in FIG. 10B) is to minimise the error signal E(z) measured by the error microphone 1024 in the headphone 1020 with reference to the hearing perception curve. The error signal is the resulting signal of the residual signal added to the cancellation signal. The error signal can be fed back into the computer device 1040 via a feedback path 1006. Thus, the amount of noise reduction provided by the ANC system at the frequency of interest can be obtained by comparing the sound pressure level difference between the primary signal and error signal in the frequency domain. Noise reduction measurements at these frequencies are compared with the target noise reduction level. If the error microphone measurement level deviates by more than a threshold, such as ±1.5 dB from the target level at any frequency in interest, the coefficient in W(z) is varied in order to achieve the target noise reduction level.

Figure 10B:
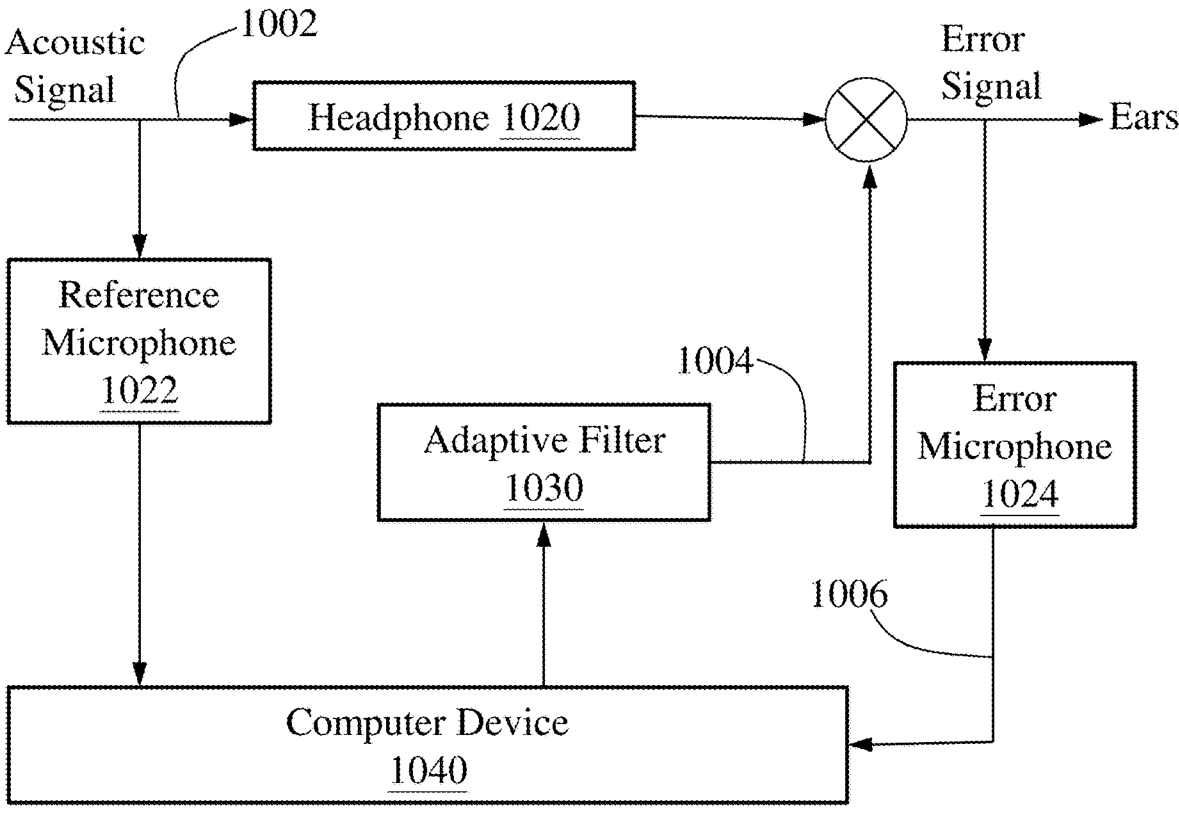
FIG. 10B illustrates the system of FIG. 10A from another perspective.

It will be appreciated that in FIG. 10B, the reference microphone 1022 and error microphone 1024 can be part of the headphone 1020. Alternatively, one or two of them can be part of the computer device 1040. Further, the computer device 1040 and the headphone 1020 can be integrated such that the computer device 1040 forms a part of the headphone 1020.

Figure 11:
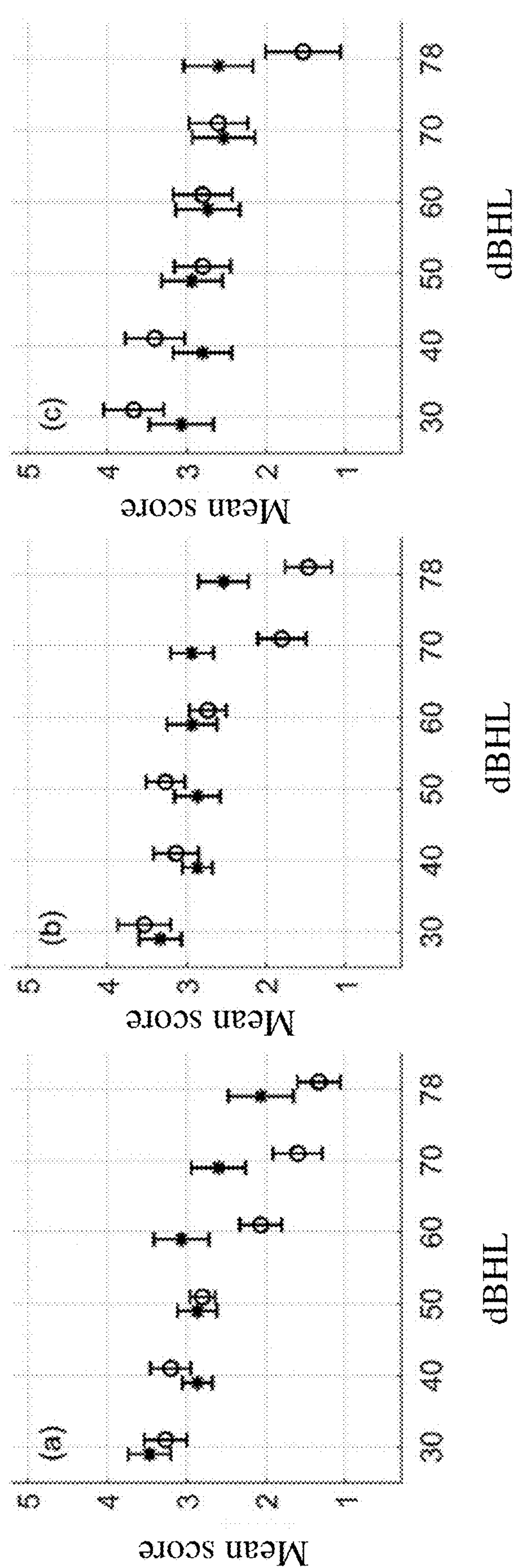
FIG. 11 illustrates comparison of aural perception response with and without ANC at different frequencies: (a) 250 Hz; (b) 500 Hz; (c) 1 kHz; (d) 2 kHz; (e) 4 kHz; (f) 8 kHz.
Figure 11:
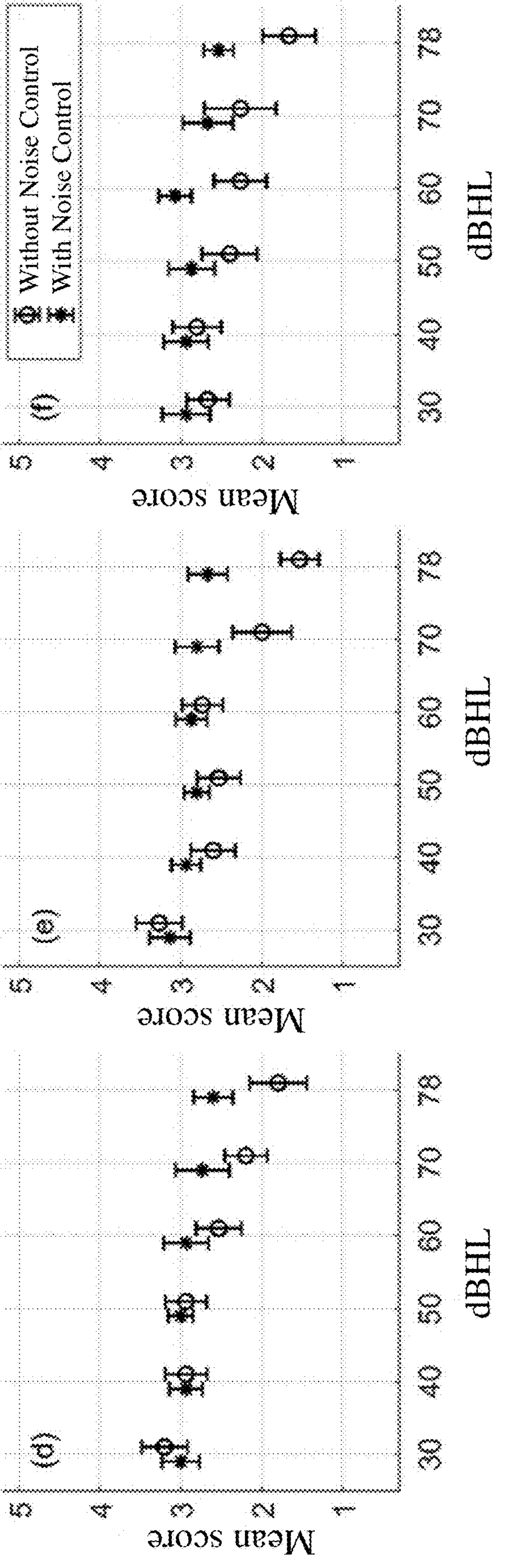

A validation test is conducted to examine the noise cancellation tuning performance based on the hearing-perception curve. The sound-presentation system, experimental environment, and procedures are similar to that of the aural perception test described above, except that the presented auditory stimuli are processed with noise attenuation according to the target curve. Some of the participants recruited for the study are invited to participate in the validation. A comparison of the aural perception responses from ASD participants subject to the original and processed sound stimuli is presented in FIG. 11. The results indicate that the proposed tuneable sonic perception method is effective especially for moderate-to-high noise levels. The aim of the target noise-reduction levels is to provide a neutral feeling or neutral response instead of achieving maximum noise reduction in the current project. It has been found that the perception score ratings remain close to the target of a neutral feeling (score of 3) across the frequencies and sound intensity hearing levels tested with the use of the proposed noise control method. A slightly larger deviation is observed at the frequency of 250 Hz compared to the other frequencies at 30 and 78 dB HL; however, an improvement is still observed in the aural perception response after applying the noise control. Similarly, better aural perception responses are observed for all the frequencies in the range of 60-78 dB HL, except for the frequency of 1 kHz. This might be related to the effective frequency range of the active and passive noise control methods. Active noise cancellation is more effective in the low-frequency range, such as at frequencies of 250 and 500 Hz. The level of noise cancellation becomes increasingly limited when the noise frequency approaches 1 kHz. Passive noise control can provide substantial noise attenuation in the high-frequency range of 2000 to 8000 Hz. The proposed tunable sonic perception method allowing for noise reduction at specific frequencies based on the characteristic aural perception of autistic participants is effective. Therefore, with such abatement of auditory stimulation, the participants with autism will perceive a comfortable aural environment that could alleviate their aversive behaviours.

As used herein, the terms “acoustic”, “aural”, “auditory” and the like are used interchangeably.

It will further be appreciated that any of the features in the above embodiments of the disclosure may be combined together and are not necessarily applied in isolation from each other. Similar combinations of two or more features from the above described embodiments or preferred forms of the disclosure can be readily made by one skilled in the art.

Unless otherwise defined, the technical and scientific terms used herein have the plain meanings as commonly understood by those skill in the art to which the example embodiments pertain. Embodiments are illustrated in non-limiting examples. Based on the above disclosed embodiments, various modifications that can be conceived of by those skilled in the art would fall within spirits of the example embodiments.

What is claimed is:

1. A method for controlling noise for a human subject, comprising:

receiving an acoustic signal by the human subject through a headphone, the acoustic signal comprising a noise signal;

generating a cancellation signal based on a hearing target curve that is related to acoustic magnitude and frequency; and applying the cancellation signal to the acoustic signal such that the noise signal is attenuated, wherein the hearing target curve comprises a relationship between noise attenuation in decibel (dB) and acoustic frequency, wherein the method further comprises:

determining a neutral response for the human subject by performing a power function curve fitting $$y_i = a(x_i^b) + c,$$

where $y_i$ is an ith mean perception rating, $x_i$ is an ith intensity level, a, b, c are coefficients;

determining, based on a hearing perception curve, a sound intensity hearing level that corresponds to the neutral response; and computing the noise attenuation based on a difference between the sound intensity hearing level and a noise level.

2. The method of claim 1, wherein the acoustic frequency is in a range from 250 Hz to 8000 Hz.

3. The method of claim 1, further comprising performing a clustering algorithm on a plurality of human subjects.

4. The method of claim 3, wherein the clustering algorithm comprises an agglomerative hierarchical algorithm.

5. The method of claim 3, further comprising performing electroencephalography test on the plurality of human subjects to obtain neural response of the plurality of human subjects in response to sound stimuli.

6. The method of claim 5, further comprising:

recording data measured by the electroencephalography test;

re-referencing the data to obtain re-referenced data;

filtering the re-referenced data to obtain filtered data; and determining a search window to identify a first peak P1, a second peak P2, and a trough point N1.

7. The method of claim 6, further comprising performing baseline correction on the filtered data.

8. The method of claim 7, further comprising averaging the filtered data in the search window.

9. The method of claim 1, further comprising:

configuring the acoustic signal such that the acoustic signal travels along a primary path and evolves into a residual signal; and performing superposition of the residual signal and the cancellation signal to generate an error signal.

10. The method of claim 9, further comprising:

measuring the error signal;

computing a difference between the acoustic signal and the error signal; and comparing the difference and the cancellation signal.

11. The method of claim 10, further comprising:

if the difference and the cancellation signal is greater than a threshold, tuning at least one parameter of an adaptive filter.

12. A system for controlling noise for a human subject, comprising:

a headphone configured to receive an acoustic signal; and a computer device configured to generate a cancellation signal based on a hearing target curve that is related to acoustic magnitude and frequency, and apply the cancellation signal to the acoustic signal such that the noise signal is attenuated, wherein the hearing target curve comprises a relationship between noise attenuation in decibel (dB) and acoustic frequency, wherein the computer device is further configured to:

determine a neutral response for the human subject by performing a power function curve fitting $$y_i = a(x_i^b) + c,$$

where $y_i$ is an ith mean perception rating, $x_i$ is an ith intensity level, a, b, c are coefficients;

determine, based on a hearing perception curve, a sound intensity hearing level that corresponds to the neutral response; and compute the noise attenuation based on a difference between the sound intensity hearing level and a noise level.

13. The system of claim 12, further comprising:

a primary path configured to transmit the acoustic signal such that the acoustic signal evolves into a residual signal; and a secondary path configured to transmit the cancellation signal, wherein superposition operation is performed for the residual signal and the cancellation signal at an intersection of the primary path and a secondary path such that an error signal is generated.

14. The system of claim 13, wherein the headphone comprises:

a reference microphone configured to measure the acoustic signal; and an error microphone configured to measure the error signal.

15. The system of claim 14, further comprising an adaptive filter disposed on the secondary path.

16. The system of claim 15, wherein the computer device is configured to compute a difference between the acoustic signal and the error signal; and compare the difference and the cancellation signal.

17. The system of claim 16, wherein the computer device is configured to tune at least one parameter of the adaptive filter when the difference and the cancellation signal is greater than a threshold.

* * * * *